United States Patent [19]

Greenlee et al.

[11] Patent Number: 4,634,715

[45] Date of Patent: Jan. 6, 1987

[54] AZA ANALOGS OF CARBOXYALKYL DIPEPTIDE DERIVATIVES AS ANTIHYPERTENSIVES

[75] Inventors: William J. Greenlee, Teaneck; Eugene D. Thorsett, Fanwood, both of N.J.

[73] Assignee: Merck & Co., Inc., Rahway, N.J.

[21] Appl. No.: 517,869

[22] Filed: Jul. 27, 1983

Related U.S. Application Data

[63] Continuation-in-part of Ser. No. 338,035, Jan. 12, 1983, abandoned, which is a continuation-in-part of Ser. No. 235,321, Feb. 17, 1981, abandoned.

[51] Int. Cl.$^4$ .................. A61K 31/40; C07D 207/04
[52] U.S. Cl. .................. 514/423; 514/307; 514/311; 514/365; 514/419; 546/147; 546/165; 548/146; 548/200; 548/201; 548/491; 548/494; 548/531; 548/532; 548/533; 560/17; 560/34; 560/51; 560/53; 560/169; 560/174; 562/507
[58] Field of Search .................. 548/533; 514/423

[56] References Cited

U.S. PATENT DOCUMENTS 4,177,277 12/1979 Ondetti et al. .................. 548/533
4,431,644  2/1984 Smith et al. .................. 548/533

OTHER PUBLICATIONS

Greenlee, et al., "Chemical Abstracts", vol. 101, 1984, col. 101:231010y.
"Chemical Abstracts", vol. 101, 1984, col. 101:151441z.
Greenlee, et al., "Chemical Abstracts", vol. 98, 1982, col. 98:89928c.

*Primary Examiner*—Glennon H. Hollrah
*Assistant Examiner*—James H. Turnipseed
*Attorney, Agent, or Firm*—Salvatore C. Mitri; Michael C. Sudol

[57] ABSTRACT

There are disclosed aza analogs of carboxyalkyl dipeptide derivatives and related compounds which are useful as converting enzyme inhibitors and as antihypertensives said compounds being represented by the general formula:

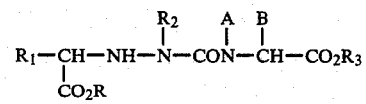

wherein A and B can be joined together to form various ring structures.

16 Claims, No Drawings

AZA ANALOGS OF CARBOXYALKYL DIPEPTIDE DERIVATIVES AS ANTIHYPERTENSIVES

This application is a continuation-in-part of application Ser. No. 338,035 filed Jan. 12, 1983 now abandoned, which, in turn, is a continuation-in-part of application Ser. No. 235,321 filed Feb. 17, 1981, now abandoned.

BACKGROUND OF INVENTION

The invention in its broad aspects relates to aza analogs of carboxyalkyl dipeptides derivatives which are useful as converting enzyme inhibitors and as antihypertensives. The compounds of this invention are represented by the following general formula:

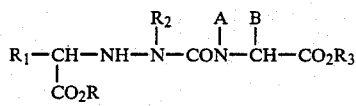

wherein:
R and $R_3$ are independently hydrogen, loweralkyl, loweralkenyl, loweralkynyl, aralkyl;
$R_1$ is aralkyl, heterocycloalkyl, substituted aralkyl and substituted heterocycloalkyl wherein the substituents in the aryl and heterocyclo groups can each independently be amino, halo, aminoloweralkyl, hydroxy, loweralkoxy, loweralkyl, loweralkenyl, and loweralkynyl; loweralkyl substituted by amino, acylamino, heteroarylamino, aryloxy, heterocyclooxy, arylthio, heterocyclothio, hydroxyl;
$R_2$ is hydrogen, loweralkyl, loweralkenyl, loweralkynyl, amino loweralkyl, amino loweralkenyl, aminoloweralkynyl, aralkyl;
A is hydrogen, cycloalkyl of 5–7 carbon atoms, aryl, heterocyclo;
B is hydrogen, loweralkyl, loweralkenyl, loweralkynyl; or,
A and B can be joined together to form ring structures which include N-CHCO$_2$R$_3$ and which have the formulae:

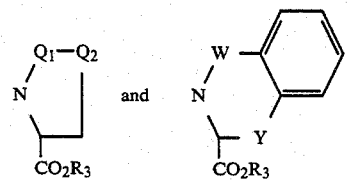

wherein:
$R_3$ is as defined above;
$Q_1$ and $Q_2$, taken together, are $CH_2CH_2$, $CH_2$—S, $CHR_4S$, $CH_2$—CH—OR$_5$ wherein $R_4$ is aryl or aryl substituted by hydroxyl, amino loweralkyl, loweralkenyl, loweralkynyl, amino, halo or alkoxy; and, $R_5$ is hydrogen, loweralkyl, loweralkenyl, loweralkynyl, aryl, aralkyl, or $CONR_6 R_7$ wherein $R_6$ and $R_7$ can each independently be hydrogen, loweralkyl, loweralkenyl, loweralkynyl, aralkyl;
W is a bond, $CH_2$;
Y is a bond, $CH_2$, $CH_2CH_2$; and,
the pharmaceutically acceptable salts thereof.
Preferred are compounds of Formula I wherein:

R and $R_3$ are independently hydrogen, loweralkyl, loweralkenyl, loweralkynyl, aralkyl;
$R_1$ is aralkyl and heterocycloalkyl wherein the alkyl groups contain 1–4 carbon atoms; substituted aralkyl, and substituted heterocycloalkyl wherein the alkyl groups contain 1–4 carbon atoms and the substituents are halo, amino, amino loweralkyl, hydroxy; substituted alkyl of 1–6 carbon atoms wherein the substituent is amino, arylamino, aryloxy, alkylthio, arylthio, heterocyclothio, or hydroxy;
$R_2$ is hydrogen, loweralkyl, amino loweralkyl;
A is cycloalkyl of 5–7 carbon atoms;
B is hydrogen; or,
A and B can be joined together to form ring structures which include NCHCO$_2$R$_3$ and which have the formula:

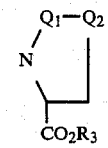

wherein:
$R_3$ is as defined above;
$Q_1$ and $Q_2$, taken together, are $CH_2CH_2$, $CH_2S$, $CHR_4S$, $CH_2CH$—OR$_5$ wherein $R_4$ is aryl or aryl substituted by hydroxyl; and, $R_5$ is lower alkyl, aralkyl.

More preferred are compounds of Formula I wherein:
R and $R_3$ are independently hydrogen, loweralkyl, aralkyl;
$R_1$ is aralkyl and heterocycloalkyl wherein the alkyl groups contain 1–4 carbon atoms; substituted aralkyl and substituted heterocycloalkyl wherein the alkyl groups contain 1–4 carbon atoms and the substituents are halo or hydroxy; substituted alkyl of 1–6 carbon atoms wherein the substituent is aryloxy or arylthio;
$R_2$ is hydrogen, loweralkyl, amino loweralkyl;
A and B can be joined together to form ring structures which include NCH—CO$_2$R$_3$ and which have the formula:

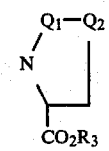

wherein:
$R_3$ is as defined above;
$Q_1$ and $Q_2$, taken together, are $CH_2CH_2$, $CH_2S$, $CHR_4S$, $CH_2CH$—OR$_5$ wherein $R_4$ is aryl or aryl substituted by hydroxyl; and $R_5$ is loweralkyl.

Most preferred are compounds of Formula I wherein:
R is hydrogen, loweralkyl;
$R_1$ is aralkyl and heterocylcoalkyl wherein the alkyl groups contain 1–3 carbon atoms; substituted aralkyl wherein the alkyl groups contain 1–3 carbon atoms and the substituents are halo or hydroxy; substituted alkyl of 1–6 carbon atoms wherein the substituent is aryloxy or arylthio;
$R_2$ is hydrogen, methyl, 4-aminobutyl;
$R_3$ is hydrogen;

A and B can be joined together to form ring structures which include NCHCO$_2$R$_3$ and which have the formula:

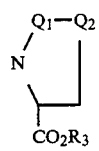

wherein R$_3$ is as defined above, and which are proline, thiaproline, or 4—carboxy2—(2—hydroxyphenyl)-thiazolidine.

The preferred, more preferred and most preferred compounds also include the pharmaceutically acceptable salts thereof.

The loweralkyl groups, except where noted otherwise, represented by any of the variables include straight and branched chain hydrocarbon radicals of from one to eight carbon atoms, for example, methyl, ethyl, propyl, isopropyl, butyl, isobutyl, t-butyl, pentyl, isopentyl, hexyl, and the like. Loweralkenyl and loweralkynyl denote alkyl groups as described above which are modified so that each contains a carbon to carbon double bond or triple bond, respectively such as vinyl, allyl, butenyl, hexynyl, and the like. The aralkyl groups represented by any of the above variables have, except where noted otherwise, from one to six carbon atoms in the alkyl portion thereof and include for example, benzyl, phenethyl, cinnamyl, and the like. Halo means chloro, bromo, iodo or fluoro. Aryl, where it appears in any of the radicals unless otherwise noted, represents phenyl, naphthyl or biphenyl. Heterocyclic groups, where they appear, have 5—6 ring atoms in the cyclic portion thereof and contain one or more N, O or S heteroatoms such as, for example, pyridyl, thienyl, furyl, indolyl, benzthienyl, imidazoyl and thiazolyl. Acyl refers to loweralknoyl and aroyl groups.

The products of Formula (I) and the preferred subgroups can be produced by one or more of the methods and subroutes depicted in the following Reaction Schemes wherein R, R$_1$, R$_2$, R$_3$, A, B, W, and Y are as defined above unless stated otherwise:

REACTION SCHEME I

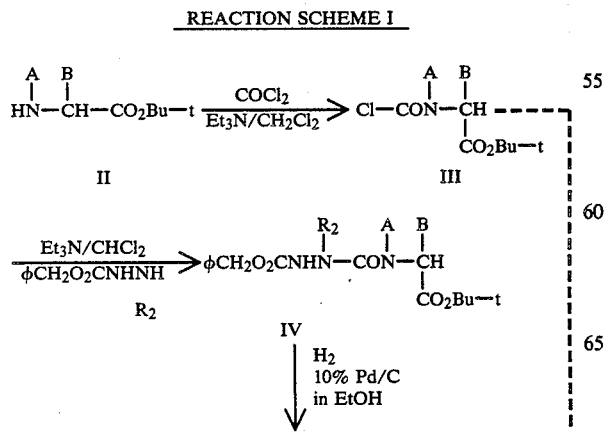

REACTION SCHEME I -continued

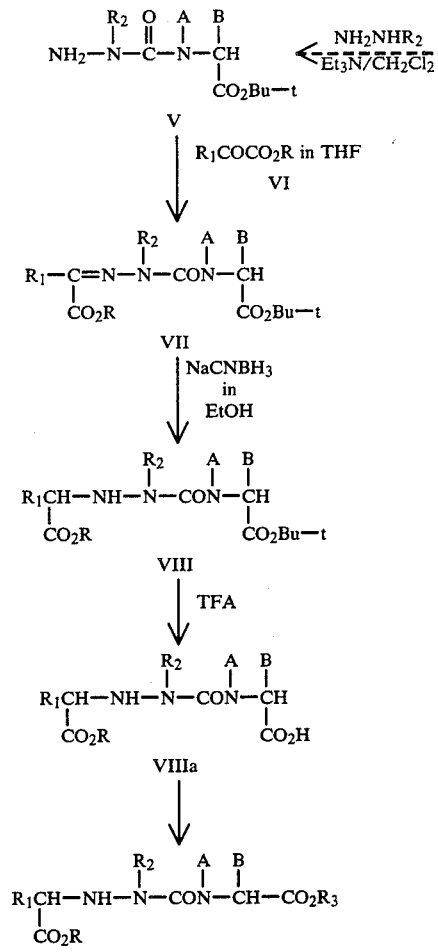

REACTION SCHEME II

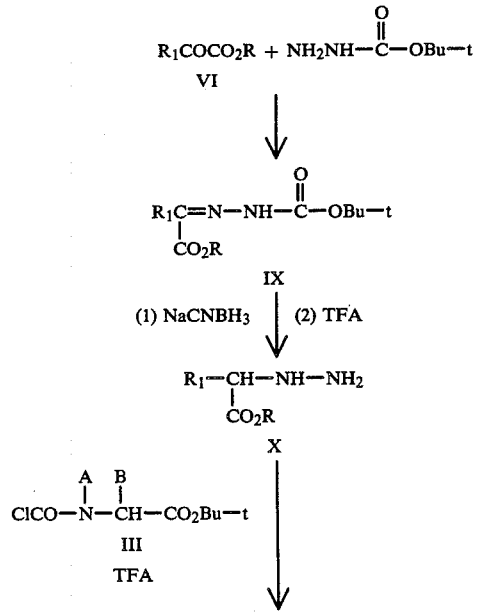

-continued
REACTION SCHEME II

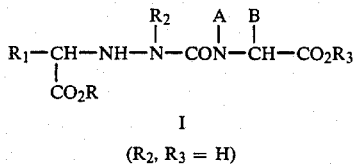

(R$_2$, R$_3$ = H)

As depicted in Reaction Scheme I, the aza analog compounds of the invention are generally produced by reacting the t-butyl ester of an imino acid II (A≠H) with phosgene in the presence of triethyl amine in methylene chloride to obtain N-chlorocarbonyl derivative III. This intermediate III, in the presence of triethyl amine in methylene chloride, can then be reacted, for example, with isopropyl or N-isopropyl-N'-carbobenzyloxy hydrazine [prepared according to known methods such as that described by C. J. Gray, et al, *Tetrahedron*, 33, 837–40(1977)] to obtain, for example by isolation, filtration and condensation, protected intermediate IV. Hydrogen, in the presence of a 10% palladium-carbon catalyst in ethanol, is reacted with IV to afford deprotected intermediate derivative V. Alternatively, III can be reacted with a substituted hydrazine in the presence of triethylamine in methylene chloride to afford V. When t-butyl esters of amino acids II (A=H) are employed, phosgene can be replaced with carbonyldiimidazole to obtain an acylimidazole intermediate which reacts as described above for the N-chlorocarbonyl derivative III. Derivative V is dissolved in tetrahydrofuran (THF) and reacted with α-keto ester or acid VI to yield an α-keto ester-carbazone VII which, after treatment with sodium cyanoborohydride in ethanol, affords the α-aza-t-butyl ester peptide derivative VIII. Peptide derivative VIII is reacted with trifluoroacetic acid (TFA) to remove the t-butyl ester group yielding VIIIa. R$_3$, when it is not hydrogen, can be introduced using R$_3$X (X=bromo, iodo) and a base such as cesium hydroxide. Removal of protecting groups, if present, then affords compounds of Formula I. Bis-esters of I can be obtained by Fisher esterification, for example, by treating Formula I compounds in an alcohol with dry HCl at room temperature.

Alternatively, compounds of Formula I when R$_2$=H can be obtained as shown in Reaction Scheme II. This procedure involves the synthesis of α-hydrazino acids or esters X followed by their condensation with N-chlorocarbonyl intermediates III. Subsequent esterification, if desired, and removal of protecting groups under standard conditions affords compounds of Formula I (R$_2$=H).

As will be evident to those skilled in the art and as demonstrated in the Examples which follow, reactive groups not involved in the condensations, such as amino, carboxy, hydroxyl, etc., may be protected by methods standard in peptide chemistry prior to the coupling reactions and subsequently deprotected to obtain the desired products.

Reactive group protection which can be employed during coupling reactions encompass known techniques such as, for example, by N-formyl, N-t-butoxycarbonyl, N-carbobenzyloxy, and 0-benzyl groups followed by their removal to yield (I). Furthermore, the R and R$_3$ functions may include removable ester groups such as benzyl, ethyl, or t-butyl.

The starting materials required for the processes of the invention are known in the literature or can be made by known methods from known starting materials.

The above described syntheses can utilize racemates or enantiomers as starting materials. When diastereomeric products result from the synthetic procedures, the diastereomeric products can be separated by chromatographic or fractional crystallization methods. The resolution of intermediates or end products if desired can be accomplished by the crystallization of salts formed from optically active acids or bases.

Many of the compounds of this invention form salts with various inorganic and organic bases which are also within the scope of the invention. Such cationic salts include alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like. Those products which contain a basic function in R$_1$ or R$_2$ also afford salts with organic and inorganic acids such s maleic acid, hydrochloric acid, and the like. The non-toxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxy-phenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.*, 125, 96 (1967).

Thus, the compounds of this invention are useful as antihypertensives in treating hypertensive mammals, including humans, and they can be utilized to achieve the reduction of blood pressure by formulating in compositions such as tablets, capsules or elixirs for oral administration or in sterile solutions or suspensions for parenteral administration. The compounds of this invention can be administered to patients (animals and human) in need of such treatment in dosages that will at least provide pharmaceutical effectiveness. Although the dose will vary depending on severity of disease, weight of patient and other factors which a person skilled in the art will recognize, the dosage range will generally be about 0.5 to 50 mg per kilo per day.

This dose range can be adjusted on a unit basis as necessary to permit divided daily dosage. Naturally, the dose will vary depending on the severity of the disease, concurrent medication and other factors which a person skilled in the art will recognize.

Also, the compounds of this invention may be given in combination with diuretics or other antihypertensives. Typically these are combinations whose individual per day dosages range from one fifth of the minimally recommended clinical dosages to the maximum recommended levels for the entities when they are given singly. To illustrate these combinations, one of the antihypertensives of this invention effective clinically in the range 5-500 milligrams per day can be effectively combined at levels ranging from 1-500 milligrams per day with the following antihypertensives and diuretics in dose ranges per day as indicated:

hydrochlorothiazide (10-200 mg), timolol (5-60 mg), methyl dopa (65-2000 mg), the pivaloyloxyethyl ester of methyl dopa (30-1000 mg), indacrinone and variable ratios of its enantiomers (25-150 mg) and (−)-4-{3-{-[2-( -hydroxycyclohexyl)ethyl]-4-oxo-2-thiazolidinyl}propyl}benzoic acid (10-100 mg).

In addition, the triple drug combinations of hydrochlorothiazide (15-200 mg) plus amiloride (5-20 mg) plus converting enzyme inhibitor of this invention (1-500 mg) or hydrochlorothiazide (15-200 mg) plus timolol (5-50 mg) plus the converting enzyme inhibitor of this invention (1-500 mg) are effective combinations to control blood pressure in hypertensive patients.

The above dose ranges will be adjusted on a unit basis as necessary to permit divided daily dosage. Also, the dose will vary depending on the severity of the disease, weight of patient and other factors which a person skilled in the art will recognize.

Typically, the compounds of this invention can be formulated into pharmaceutical compositions as described below.

About 5 to 500 mg. of a compound or compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples, which are at both carbon atoms bearing $R_1$ and $CO_2R_3$ of the natural L-amino acid configuration, are isolated by column chromatography or fractional crystallization. In most cases, these preferred absolute configurations can also be designated (S)-.

In the following Examples, NMR chemical shifts are reported in ppm downfield from tetramethyl silane as internal standard. Optical rotations were measured in methanol solution.

EXAMPLE 1

α-Azaalanyl-(L)-proline t butyl ester (2)

A solution of proline t-butyl ester (10.0 g; 0.058 mol) and triethylamine (8.56 ml; 6.22g; 0.0614 mol) in dry THF (60 ml) was added to a cold (0° C.) solution of phosgene (12.5%) in benzene (61 ml; 0.070 mol) over 1 hour. An additional 50 ml of dry THF was added and stirring was continued for 2 hours. The reaction mixture was filtered and evaporated, giving N-chlorocarbonyl-(L)-proline t-butyl ester [1] as a dark-red oil (13.35 g).

A solution of crude carbamoyl chloride 1 (9.35 g) in dry THF (40 ml) was added to an ice-cold solution of methylhydrazine (3.46 g; 4.00 ml; 0.075 mol) and triethylamine (6.33 g; 8.73 ml; 0.063 mol) in dry THF (40 ml). Stirring was continued at room temperature for 18 hours. The reaction mixture was filtered and evaporated, giving a light yellow solid. Recrystallization from hexane - chloroform gave 2 (6.62 g; 0.0272 mol; 68%) as a white solid, mp 89°-92°, TLC (silica gel; $CH_2CL_2$—$CH_3OH$, 10:1) Rf=0.45. MS m/e 243 (M+) Analysis: Calculated for $C_{11}H_{21}N_3O_3$; C,54.30; H, 8.70; N, 17.27. Found: C, 54.45; H, 8.96; N, 17.29, NMR ($CDCl_3$): δ1.42 (9H,S); 1.7-2.3(4H.S); 3.00 (3H,S); 3.4-3.8(2H,m); 3.8(2H.bs); 4.4(1H.m) 1R($CHCl_3$): 35-3300, 1730, 1630 cm$^{-1}$ $[\alpha]_D = -55.7° \pm 0.5°$.

EXAMPLE 2

α-Azaglycinyl-(L)-proline t-butyl ester (3)

A solution of carbamoyl chloride 1 (1.00 g; from above) in dry THF (3.5 ml) was added over 10 minutes to an ice-cold solution of anhydrous hydrazine (0.269 g; 0.310 ml; 8.40 mmol) and triethylamine (0.708 g; 0.975 ml; 7.00 mmol) in dry THF (4 ml). Stirring was continued overnight at room temperature. The mixture was filtered and evaporated to a light yellow solid. Recrystallization from hexanes-ethyl/acetate gave pure carbazide 3 (0.533 g; 2.33 mmol; 52%) as a white solid, mp 83°-84° C. TLC (silica gel; $CH_2Cl_2$—$CH_3OH$, 10:1)Rf=0.25-0.35. MS m/e 173 (M+-56). Analysis: Calculated for $C_{10}H_{19}N_3O_3$: C, 52.39; H, 8.35; N, 18.33.

Found: C, 52.08; H, 8.58; N, 18.01; NMR (CDCl$_3$); δ1.43 (9H.S); 2.0–2.3 (4H,m); 3.1–3.4(2H,m); 3.8(2H,bs): 4.3–4.6(1H,m); 6.2(1H,bs); IR(CHCl$_3$): 3500–3300, 1730, 1660, 1640 cm$^{-1}$. $[\alpha]_D = -46.5 \pm 0.5°$.

EXAMPLE 3

N-Carbobenzyloxy-N'-isopropylhydrazine (4)

Acetone (0.377 g; 0.477 ml; 6.50 mmol) was added to a solution of carbobenzyloxyhydrazine (1.00 g; 6.02 mmol) in absolute ethanol (6 ml). After one hour, the solution was concentrated to dryness and then ethanol (5 ml) and sodium cyanoborohydride (0.19 g; 3.0 mmol) were added. The mixture was stirred for 18 hours and then evaporated to a thick syrup. Hydrochloric acid (0.50 N; 5 ml) and ether (50 ml) were added and the two-phase mixture was stirred for one hour. The aqueous layer was neutralized by addition of solid NaHCO$_3$ and extracted with ether (2×25 ml). The combined ether portions were washed with water and brine and dried (MgSO$_4$) Removal of solvent gave a solid which was recrystallized from hexanes - ether, giving pure hydrazide 4 (1.09 g; 5.25 mmol; 87%), mp 61°–62°. TLC (silica gel; CH$_2$Cl$_2$—CH$_3$OH; 20:1) Rf=0.5. MS m/e 208 (M+). Analysis: Calculated for C$_{11}$H$_{16}$N$_2$O$_2$: (C, 63.44; H, 7.44; N, 13.45). Found: C, 63.22; H, 7.67; N, 13.71; NMR (CDCl$_3$);δ0.97 (6H,d,J=6); 3.15 (1H, septet, J=6); 3.8–4.6(1H, broad); 5.13(2H,S); 6.2–7.0(1H, broad); 7.33 (5H,S); IR(CHCl$_3$) 3500, 1720 cm$^{-1}$.

EXAMPLE 4

α-Azavalinyl-(L)-proline t - butyl ester (5)

Carbamoyl chloride 1 (4 mmol, crude), prepared as described above, was combined with carbazide 4 (3.50 mmol; 0.728 g) and triethylamine (0.557 ml; 4.00 mmol) in dry THF (2 ml). The mixture was heated at reflux for 7 hours, then filtered and evaporated to a thick oil. This was dissolved in benzene (10 ml) and hydrogenated with 10% Pd(C) (0.35 g) at 1 atm. for 6 hours. Filtration of the catalyst and evaporation gave a light yellow oil which was purified by flash chromatography on silica gel (CH$_2$Cl$_2$—CH$_3$OH, 50:1). There was obtained pure carbazide 5 (0.622 g; 2.30 mmol; 66%) as a light yellow solid. Recrystallization from hexanes gave a sample, mp 87°–91° C. TLC (silica gel; CH$_2$Cl$_2$—CH$_3$OH; 20:1) Rf=0.4. MS m/e 271 (M+). Analysis: Calculated for C$_{13}$H$_{25}$N$_3$O$_3$: C, 57.54; H, 9.29; N, 15.48. Found: C, 57.67; H, 9.46; N, 15.44. NMR (CDCl$_3$): δ1.08 (3H,d, J=6); 1.13 (3H, d, J=6); 1.43 (9H,s); 1.7–2.2 (4H,m); 2.4–2.7 (2H,m); 3.3 (2H,bs); 4.07 (1H, septet, J=6); 4.3–4.5 (1H,m). IR(CHCl$_3$): 3600–3300, 1730, 1630 cm$^{-1}$. $[\alpha]_D = 15.9° \pm b\ 0.5°$. $[\alpha]_d = 15.9° \pm 0.5°$.

EXAMPLE 5

N-t-BOC-2-pyrrolidinol (6)

Di-t-butyl dicarbonate (2.3 ml; 10 mmol) was added dropwise to a solution of 4-aminobutyraldehyde diethyl acetal (1.73 ml; 10 mmol) in chloroform (20 ml). Warming of the solution and evolution of a gas were observed. After 10 minutes, TLC (silica gel, CH$_2$Cl$_2$—CH$_3$OH, 20:1) showed complete consumption of the starting amine and a single product spot, Rf=0.8. Solvent was removed, giving a colorless oil.

The crude product was dissolved in a mixture of THF (30 ml) and hydrochloric acid (0.50 N, 30 ml). Stirring was continued for 2 hours. Then the mixture was diluted with brine (50 ml) and extracted with ether (3×25 ml). The combined ether portions were washed with water, saturated bicarbonate, and brine, and dried (MgSO$_4$). After removal of solvent, the colorless oil was purified by chromatography on silica gel (Baker; 2×18 cm) in hexanes - ether (2:1), giving pure 6 (0.35 g, 1.87 mmol, 19%) as a colorless oil. TLC (silica gel, hexanes-ether, 2:1) Rf=0.5. MS m/e 170 (M+-OH). NMR (CDCl$_3$): δ1.48 (9H,S); 1.8–2.1 (4H,m); 3.2–3.7 (2H,m); 4.2–4.4 (1H, broad); 5.4–5.6 (1H, broad). IR (CHCl$_3$): 3700–3400, 3000, 2920, 1675 cm$^{-1}$.

EXAMPLE 6

N-(t-Boc-4-amino-1-butyl)-N'-CBZ-hydrazine (8)

A solution of N-t-Boc-2-pyrrolidinol (0.187 g; 1.00 mmol) and carbobenzyloxyhydrazine (0.166 g; 1.00 mmol) were combined with dry THF (2 ml) and the resulting solution was heated at reflux for 2 hours. TLC (silica gel; hexanes - EtAc, 2:1) showed two carbazone isomers 7a,7b, Rf=0.2, 0.3. The mixture was evaporated to dryness and the residue was combined with ethanol (3 ml) and sodium cyanoborohydride (63 mg; 1.00 mmol). The solution was stirred for 3 hours and then the solvent was evaporated and replaced with hydrochloric acid (0.50N, 3 ml) and ether (15 ml). The two-phase mixture was stirred for 30 min. and then the aqueous layer was neutralized with solid NaHCO$_3$ and extracted with ethyl acetate (3×10 ml). The combined organic portions were dried (MgSO$_4$) and solvent was removed, giving a light yellow oil. Chromatography on silica gel (Baker, 1×20 cm) in hexanes - EtAc (2:1) gave pure carbazide 8 (0.155 g; 0.46 mmol; 46%) which was recrystallized from hexanes-EtAc, mp 73°–74°. TLC (silica gel; hexanes -EtOAc; 2:1) Rf=0.25. MS m/e 281 (M+-56). Analysis: Calculated for C$_{17}$H$_{27}$N$_3$O$_4$: C, 60.51; H, 8.06; N, 12.45. Found: C, 60.18; H, 8.11; N, 12.26 NMR (CDCl$_3$): δ1.42 (9H, s); 2.8–3.3 (4H,m); 3.9–4.1 (1H, broad); 4.8–5.0 (1H, broad); 5.17 (2H,s); 6.7–6.9 (1H, broad); 7.37 (5H,s); 1R (CHCl$_3$) 3500, 2980, 1720 cm$^{-1}$.

EXAMPLE 7

N -t-Boc-α-Azalysyl-(L)-proline t-butyl ester (10)

A solution of carbazide 8 (0.941 g; 2.79 mmol) and carbamoyl chloride 1 (4 mmol.; crude) in dry THF (7 ml) containing triethylamine (0.56 ml; 4.00 mmol) was warmed at reflux for 8 hours. TLC (silica gel, hexanes-EtAc, 1:1, 2 developments) showed a single product (9), Rf=0.5. The residue after filtration and evaporation of solvent was dissolved in a mixture of ethyl acetate (10 ml) and acetic acid (3 ml) and hydrogenated at 1 atm with 10% Pd(C) (0.20 g) for 4 hours. The crude product was purified by flash chromatography on silica gel (E. Merck No. 9385, 1.5×22 cm) in hexanes-EtOAc (2:1), giving pure carbazide 10 (0.579 g; 1.45 mmol; 52%) as a colorless oil. TLC (silica gel, EtOAc) Rf=0.3. MS m/e 400 (M+). NMR (CDCl$_3$): δ1.43 (18H,s); 1.8–2.1 (8H,m); 3.0–3.8 (8H,m); 4.3–4.7 (1H,m); 4.8–5.1 (1H, broad). IR (CHCl$_3$): 3600–3300, 1730 (shoulder), 1720, 1630 cm$^{-1}$.

EXAMPLE 8

α-Azaalanyl-(L)-phenylalanine t-butyl ester (11)

Triethylamine (0.28 ml; 2 mmol) was added to a slurry of (L)-phenylalanine t-butyl ester hydrochloride (0.50 g; 1.94 mmol) in methylene chloride (4 ml). Carbonyldiimidazole (0.325 g; 2 mmol) was added, and stirring was continued for 30 minutes. Then methylhydrazine (0.11 ml; 2 mmol) was added over 5 minutes. Stirring was continued for 18 hours. Solvent was removed, and the resulting solid residue was partitioned between ether and water. The ether layer was washed twice with water and once with brine, and dried (MgSO$_4$). Removal of solvent gave crude carbazide 11 as a colorless oil. Flash chromatography on silica gel (E. Merck No. 9385; 2×12 cm) in 100:1 methylene chloride: methanol gave pure 11 (0.480 g; 1.63 mmol; 84%): TLC (20:1 CH$_2$Cl$_2$:CH$_3$OH) Rf=0.3. MS m/e 294 (M+). Analysis: Calculated for C$_{15}$H$_{24}$N$_3$O$_3$: C, 61.20 H, 8.22 N, 14.27. Found: C, 61.75 H, 8.28 N, 14.00. NMR (CDCl$_3$) δ1.33 (9H,s); 3.00 (3H,s); 3.05 (2H,d,J=6); 3.6 (2H,bs); 4.63 (1H,d of t; J=8,6); 6.7–7.0 (1H, m); 7.25 (5H,s); IR (CHCl$_3$): 3450, 3000, 1730, 1650 cm$^{-1}$.

EXAMPLE 9

α-Azaphenylalanyl-(L)-proline t-butyl ester (12)

Carbamoyl chloride 1 was prepared as before from (L)-proline t-butyl ester (10 g), giving a light-red oil (15.7 g). This was added as a solution in THF (50 ml) to an ice-cold mixture consisting of benzylhydrazine dihydrochloride (0.029 mol; 5.7 g), triethylamine (0.088 mol; 12.2 ml) and THF (40 ml). The mixture was stirred at room temperature for 18 hours. Filtration and removal of solvent gave the crude product as a thick syrup. This was purified by flash chromatography on silica gel (E. Merck No. 9385; 3×30 cm) in CH$_2$Cl$_2$—CH$_3$OH (100:1). Fractions containing pure carbazide 12 were combined, giving 4.06 g (0.0127 mol; 44%). Early fractions contained a small amount of an isomeric carbazide 13, but this was not fully characterized. TLC (20:1 CH$_2$Cl$_2$:CH$_3$OH) Rf=0.5. MS m/e 319 (M+). NMR (CDCl$_3$) δ1.42 (9H,s); 1.8–2.2 (4H, m); 3.4–3.5 (2H,bs); 3.5–3.8 (2H,m); 4.3–4.6 (1H, m); 4.62 (2H,s); 7.3–7.4 (5H,s). IR (CHCl$_3$): 3000, 1740, 1630 cm$^{-1}$.

EXAMPLE 10

N-(1-Carbobenzyloxy-3-phenylpropyl)-α-azaalanyl-(L)-proline t-butyl esters-(14R, 14S)

Carbazide 2 (0.243 g; 1.00 mmol) and benzyl 4-phenyl-2-oxobutanoate (0.268 g; 1.00 mmol) were combined with THF (2 ml) and 2 drops of glacial acetic acid and the resulting solution was warmed at 60° for one hour. After the mixture had been stirred overnight at room temperature, it was evaporated to a thick, yellow syrup. TLC (silica gel; CH$_2$Cl$_2$—CH$_3$OH 20:1) showed a single product spot at Rf=0.6. To a solution of the crude product in absolute ethanol (3 ml) was added sodium cyanoborohydride (63 mg; 1.00 mmol). After 3 hours the ethanol was evaporated and the residue was combined with dilute hydrochloric acid (0.5 N, 3 ml) and ethyl acetate (15 ml). The two-phase mixture was stirred vigorously for one hour and then the aqueous phase was neutralized by addition of solid potassium carbonate and extracted three times with ethyl acetate. The combined organic portions were washed with water and brine and dried (MgSO$_4$). Removal of solvent gave a thick, colorless oil. TLC (silica gel; hexanes-ethyl acetate 2:1; 2 developments) showed two diastereomers, Rf=0.25, 0.30. Separation of the two was achieved by chromatography on silica gel (E. Merck 60B; 6.5 ml/min) at medium pressure in hexanes-ethyl acetate (4:1).

The following were obtained:

(1) 14S; more-mobile diastereomer (158 mg). MS m/e 495 (M+). NMR (CDCl$_3$) δ1.42 (9H,s); 1.8–2.3 (6H,m); 2.5–2.9 (2H,m); 2.90 (3H,s); 3.1–3.6 (3H,m); 4.3–4.6 (1H,m); 5.0 (1H, broad); 5.10 (2H,s); 7.10 (5H,s); 7.28 (5H,s). IR (CHCl$_3$): 3000, 1740, 1640 cm$^{-1}$.

(2) Mixed fractions 53.5 mg.

(3) 14R; less mobile diastereomer (170 mg) mp 76°–79° (hexanes-EtAc) MS m/e 495 (M+). NMR (CDCl$_3$) δ1.42 (9H,s); 1.7–2.2 (6H,m); 2.5–2.9 (2H,m); 2.92 (3H,s); 3.1–3.6 (3H,m); 4.2–4.5 (1H,m); 5.07 (2H,s); 5.1–5.3 (1H,broad); 7.10 (5H,s); 7.27 (5H,s). IR (CHCl$_3$): 3000, 1740, 1640 cm$^{-1}$. (A total of 382 mg; 0.771 mmol; 77%). Analysis: Calculated for C$_{28}$H$_{37}$N$_3$O$_5$: C, 67,86; H, 7.52; N, 8.48. Found: C, 67.74; H, 7.39; N, 8.29.

EXAMPLE 11

N-(1-Carbobenzyloxy-3-phenylpropyl)-α-azaalanyl-(L)-prolines (15R, 15S)

A solution of the more mobile azapeptide ester 14S (158 mg) in trifluoroacetic acid (10 ml) was allowed to stand for 3 hours. The solution was evaporated to dryness, and then an ether solution of the residue was washed several times with water and dried (MgSO$_4$). Removal of solvent gave a thick residue which was purified on a column of LH-20 (in methanol) to give 118 mg of azapeptide 15S as a colorless oil. TLC (silica gel; ethyl acetate-pyridine-acetic acid-water (EPAW) 20:5:1:1) Rf=0.6.

NMR (CDCl$_3$) δ1.7–2.3 (6H,m); 2.5–2.9 (2H,m); 2.95 (3H,s); 3.3–4.2 (3H,m); 4.4–4.8 (1H,m); 5.3 (2H,s); 7.1–7.4 (5H,m); 7.30 (5H,s).

The less mobile azapeptide diastereomer 14R (170 mg) was treated in an identical manner, and the resulting product was purified by chromatography on LH-20 (in methanol), giving 92 mg of pure azapeptide 15R. TLC (silica gel; EPAW 20:5:1:1) Rf=0.6.

NMR (CDCl$_3$) δ1.6–2.2 (6H,m); 2.5–2.9 (2H.m); 3.08 (3H,s); 3.3–3.6 (2H,m); 3.8–4.1 (1H,m); 4.7–4.9 (1H,m); 5.02 (2H,s); 5.8–6.0 (1H,broad); 7.1–7.3 (5H,m); 7.18 (5H,s).

EXAMPLE 12

N-(1-Carboethoxy-3-phenylpropyl)-α-azaalanyl-(L)-proline t-butyl esters (16R, 16S)

Using the procedure described in Example 11 above, carbazide 2 (0.486 g; 2.00 mmol) and ethyl 4-phenyl-2-oxobutanoate (0.412 g; 2.00 mmol) were used to prepare azapeptide 15 (R,S), which was purified by flash chromatography on silica gel (E. Merck, No. 9385; 2×25 cm) in CH$_2$Cl$_2$—CH$_3$OH (100:1). The product (0.753 g, 1.74 mmol; 87%) was a colorless oil. Separation of diastereomers was achieved on a column (3×18 cm) of E. Merck silica gel H (Acc. to Stahl), slurry-packed in hexanes-EtAc (3:1) by pipette. More mobile isomer (116 mg), less-mobile isomer (75.4 mg) and mixtures of the two (300 mg) were obtained. More mobile isomer 16S: TLC (silica gel, hexanes-EtAc, 2:1, 2 developments, Rf=0.30. MS m/e 433 (M+). NMR (CDCl$_3$): 1.25 (3H,t,J=7); 1.43 (9H,s); 1.7–2.3 (6H, m); 2.6–3.0 (2H,m); 2.95 (3H,s); 3.4–3.7 (3H,m); 4.12 (2H,q,J=7); 4.45 (1H, broad q, J=6); 4.8–5.0 (1H, broad); 7.2–7.4 (5H, bs); IR (CHCl$_3$): 1730, 1640 cm$^{-1}$. Less mobile isomer (16R): TLC, Rf=0.25. MS: m/e 433 (M+), NMR (CDCl$_3$): δ1.23 (3H, t, J=7); 1.42 (9H,s); 1.8–2.4 (6H, m); 2.6–3.0 (2H,m); 2.95 (3H,s); 3.4–3.7 (3H,m); 4.12 (2H, q, J=7); 4.3–4.5 (1H,m); 5.0–5.3 (1M, broad); 7.2–7.4 (5H, bs). IR (CHCl$_3$): 1730, 1640 cm$^{-1}$.

EXAMPLE 13

N-(1-Carboethoxy-3-phenylpropyl)-α-azaalanyl-(L)-prolines (17R, 17S)

Each diastereomer of azapeptide was treated as described in Example 11 above with trifluoroacetic acid with the following results. Azapeptide 16S (0.116 g; 0.238 mmol) gave azapeptide 17S (0.0448 g; 0.119 mmol; 50%) after purification on LH-20 (in methanol). TLC (silica gel, EPAW, 20:5:1:1) Rf=0.65.MS m/e 449 (M+-monotrimethylsilyl) NMR (CDCl$_3$): 1.28 (3H, t, J=7); 1.8–2.4 (6H,m); 2.5–2.9 (2H,m); 3.07 (3H,s); 3.5–4.0 (3H,m); 4.17 (2H,q, J=7); 4.3–4.7 (1H,m); 7.23 (5H,bs); IR (CHCl$_3$): 3500–2900; 1740; 1670 cm$^{-1}$. Azapeptide 16R (0.0754 g; 0.174 mmol) gave azapeptide 17R (0.0398; 0.106 mmol; 61%) after purification on LH-20. TLC, RF=0.65. Ms m/e 449 (M+-monotrimethylsilyl). NMR (CDCl$_3$): δ1.28 (3H, t, J=7); 1.8–2.4 (6H,m); 2.7–3.0 (2H,m); 3.10 (3H,s); 3.5–4.0 (3H, m); 4.17 (2H, q, J=7); 4.5–4.9 (1H,m); 7.15 (5H,m), IR (CHCl$_3$): 3500–2900; 1740, 1670 cm$^{-1}$.

EXAMPLE 14

N-(1-Carboxy-3-phenylpropyl)-α-azaalanyl-(L)-proline t-butyl ester (18)

A solution of carbazide 2 (0.243 g; 1.00 mmol) and 4-phenyl-2-oxobutanoic acid (0.534 g; 3.00 mmol) in water (1 ml) was adjusted to pH=7 by addition of aqueous sodium hydroxide (2N). Then a solution of sodium-cyanoborohydride (0.0628 g; 1.00 mol) in water (1 ml) was added over a period of 4 hours. Stirring was continued for 48 hours. Water-washed DOWEX® 50W-X4 resin (3 g) was added and stirring was continued for 90 minutes. The mixture was then diluted with water-CH$_3$OH(1:1; 5 ml) and transferred to a column of the same resin (5 g). Elution was carried out with H$_2$O—CH$_3$OH (10:1) and then H$_2$O-pyridine (50:1). The latter solvent mixture brought about elution of pure azapeptide ester 18 (0.300 g; 0.742 mmol; 74%) as a white foam after freeze-drying. TLC (silica gel; EPAW, 20:5:1:1), RF=0.6. MS m/e 477 (M+, monotrimethylsilyl). NMR (CDCl$_3$); δ1.43 (9H,S); 1.7–2.3 (6H,m); 2.6–3.0 (2H,m); 3.00 (3H,s); 3.4–3.7 (2H,m); 4.3–4.6 (1H,m); 7.20 (5H,s); 7.25 (2H,bs).

EXAMPLE 15

N-(1-Carboxy-3-phenylpropyl)-α-azaalanyl-(L)-proline (19)

A solution of azapeptide ester 18 (0.301 g; 0.742 mmol) in EtAc (2 ml) was added by syringe to an ice-cold solution of anhydrous hydrogen chloride in EtAc (5 ml; 5.16 N). Stirring was continued for 2 hours at room temperature, and then the solution was evaporated to a white solid. Purification was carried out on DOWEX® 50W-X4 resin (7 g) by eluting with H$_2$O—CH$_3$OH (1:1, then 10:1) and then H$_2$O-pyr (50:1). The latter solvent mixture brought about elution of azapeptide 19 (0.100 g; 0.287 mmol; 39%) as a white foam. Further purification by chromatography on a column of LH-20 (in CH$_3$OH) gave pure azapeptide 19 (71 mg) as a white foam. TLC (silica gel; EPAW, 10:5:1:3) RF=0.5.

EXAMPLE 16

N-(1-Carboxyethyl)-α-azaalanyl-(L)-proline-t-butyl ester (20)

A solution of carbazide 2 (0.486 g; 2.00 mmol) and sodium pyruvate (1.10 g; 10 mmol) in water (30 ml) was stirred for 15 minutes. A solution of sodium cyanoborohydride (0.251 g; 4.00 mmol) in H$_2$O (2 ml) was added over 4 hours. Stirring was continued for 18 hours. Then 5 g of DOWEX® 50W-X4 resin (H$_2$O-washed) was added, and the mixture was stirred for 4 hours. The mixture was added to a column of the same resin (5 g) and eluted with H$_2$O—CH$_3$OH (10:1) and then H$_2$O-pyr (50:1). The latter solvent caused elution of pure azapeptide 20 (0.504 g; 1.60 mmol; 80%) which was freeze dried to a white foam. TLC (silica gel; EPAW 20:5:1:1) Rf=0.7. NMR (CDCl$_3$) δ1.30 (3H, d,J=7), 1.45 (9H,s); 1.8–2.3 (4H,m); 3.03 (3H,s); 3.5–3.9 (3H,m); 4.4–4.7 (1H,m); 8.2–8.5 (1H,broad).

EXAMPLE 17

N-(1-Carboxyethyl)-α-azaalanyl-(L)-proline (21)

A solution of azapeptide 20 (0.504 g; 1.60 mmol) in ethyl acetate (2.5 ml) was added to an ice-cold solution of hydrogen chloride in ethyl acetate (7.5 ml; 5.2 N). The resulting solution was stirred at room temperature for 4 hours. Removal of solvent gave a white, solid residue. Purification of this solid on DOWEX® 50W-X4 (7.5 g) with H$_2$O-pyr (50:1) as eluant gave, after freeze drying, pure azapeptide 21 (0.290 g; 1.12 mmol; 70%) as a white foam. Purification of a portion of this material (50 mg) on a column of LH-20 (in methanol) gave azapeptide 21 as a colorless oil (20.0 mg). TLC (silica gel, EPAW, 10:5:1:3) Rf=0.25, 0.30 (2 diastereomers).

EXAMPLE 18

N-(1-Carboxy-4-3-methylbutyl)-α-azaalanyl-(L)-proline-t-butyl ester (22)

To a solution of carbazide 2 (0.468 g; 2.00 mmol) and 4-methyl-2-oxopentanoic acid (1.52 g, 10.0 mmol) in H$_2$O (4 ml) was added over 7 hours a solution of sodium cyanoborohydride (0.251 g; 4.00 mmol) in H$_2$O (2 ml). Stirring was continued for 18 hours. Water-washed DOWEX® 50W-X4 resin (7.5 g) was added to the mixture (pH=2) and vigorous stirring was continued for 2 hours. Then the entire mixture was transferred to a column of DOWEX® resin (5 g) using H$_2$O—CH$_3$OH (1:1) to dissolve some insoluble material remaining in the flask. The column was eluted with H$_2$O—CH$_3$OH (1:1, then 10:1) and then H$_2$O-pyr (50:1). This last solvent caused elution of pure azapeptide 22 (0.596 g; 1.67 mmol; 84%) which was a white foam after freeze-drying. TLC (silica gel; EPAW, 20:5:1:1) Rf=0.80, 0.85 (2 diastereomers). MS m/e 429 (M+, monotrimethylsilyl). NMR (CDCl$_3$): δ0.95 (6H, d, J=6); 1.38 (9H, s); 1.8–2.2 (7H,m); 3.03 (3H,s); 3.3–3.6 (3H,m); 4.2–4.5 (1H,m); 7.6–7.8 (2H, broad). IR (CHCl$_3$): 3600–2500, 1740, 1650 cm$^{-1}$.

EXAMPLE 19

N-(1-Carboxybutyl)-α-azaalanyl-(L)-proline (23)

A solution of azapeptide 22 (74.4 mg; 0.208 mmol) in trifluoroacetic acid (2 ml) was allowed to stand for 2 hours. Then solvent was evaporated and the residue was purified on DOWEX® 50W-X4 resin (3 g). Elution with H₂O-pyr (50:1) gave azapeptide 23 (56.9 mg; 0.189 mmol, 91%); as a white foam. Further purification of a column of LH-20 (in CH₃OH) gave 28.3 mg of a white foam. TLC (silica gel; EPAW, 10:5:1:3) Rf=0.5, 0.6 (2 diastereomers). MS m/e 445 (M+, bistrimethylsilyl): NMR (CDCl₃): δ0.98 (6H, d, J=6); 1.4–1.8 (2H,m); 1.8–2.3 (5H,m); 3.10 (3H,s); 3.4–3.8 (3H,m); 4.3–4.7 (1H,m); 9.0–9.7 (3H, broad). IR (CHCl₃): 3600–2500; 1720, 1670, 1610 cm⁻¹.

EXAMPLE 20

N-(1-Carbobenzyloxy-5-phthalimidopentyl)-α-azaalanyl-(L)-proline-t-butyl ester (24)

A solution of carbazide 2 (0.665 g; 2.74 mmol) and benzyl 6-phthalimido-2-oxohexanoate (1.00 g; 2.74 mmol) in THF (5 ml) containing glacial acetic acid (3 drops) was heated at reflux for 3 hours. TLC (silica gel, CH₂Cl₂—CH₃OH,20:1) showed a single product spot, Rf=0.5. The crude product was treated as for 14 (Example 10) with sodium cyanoborohydride (172 mg; 2.74 mmol), giving pure carbazide 24 (1.18 g; 2.00 mmol; 73%) after flash chromatography on silica gel (hexanes-EtAc, 1:1). TLC (silica gel; hexanes-EtOAc, 1:1) showed a mixture (1:1) of diastereomers, Rf=0.25, 0.30. MS m/e 592 (M+). Analysis: Calculated for C₃₂H₄₀N₄O₇: C, 64.85; H, 6.80; N, 9.45. Found: C, 64.24; H, 6.98; N, 8.95. NMR (CDCl₃): δ1.40 (9H,s); 1.5–2.0 (8H,m); 2.88, 2.90 (3H,2 x S); 3.2–3.7 (6H,m); 4.2–4.4 (1H,m); 4.8–5.1 (1H,m); 5.12, 5.15 (2H,2 x·S); 7.27 (5H,s); 7.6–7.9 (4H,m). IR (CHCl₃): 2980, 1770, 1730, 1720, 1640 cm⁻¹.

EXAMPLE 21

N-(1-Carboxy-5-phthalimidopentyl)-α-azaalanyl-(L)-proline-t-butyl ester (25)

A solution of azapeptide ester 24 (0.402 g; 0.679 mmol) in ethyl acetate (5 ml) and acetic acid (0.2 ml) was hydrogenated with 110 mg of 10% Pd C for 18 hours. Filtration of catalyst and removal of solvent gave azapeptide 25 as a white foam (0.330 g). TLC (silica gel; EPAW 20:5:1:1) Rf=0.7. MS m/e 574 (M+, monotrimethylsilyl). NMR (CDCl₃): δ1.42 (9H.s); 1.5–2.1 (10H,m); 3.00 (3H,s); 3.4–3.8 (5H,m); 4.3–4.6 (1H,m); 7.6–7.8 (4H,m); 7.8–8.0 (1H, broad).

EXAMPLE 22

N-(5-Amino-1-carboxypentyl)-α-azaalanyl-(L)-proline (27)

To a solution of the crude azapeptide 25 (0.330 g) in ethanol (4 ml) was added anhydrous hydrazine (1.70 mmol; 0.054 g). After 3 hours, the mixture was filtered to remove the white precipitate and evaporated to a white foam. Purification on DOWEX® 50W-X4 (7.5 g) using H₂O-pyr (50:1) as eluant, gave N-(5-amino-1-carboxypentyl)-α-azalanyl-(L)-proline-t-butyl ester (26) as a white foam (0.264 g). TLC (silica gel; EPAW 10:5:1:3) Rf=0.25, MS m/e 516 (M+, bistrimethylsilyl).

A solution of the azapeptide ester 26 (0.264 g) in trifluoroacetic acid (5 ml) was allowed to stand for 2 hours. Solvent was removed, and the light-brown residue was chromatographed on DOWEX® 50W-X4 (10 g) using H₂O-pyr (50:1) as eluant. There was obtained 0.166 g of azapeptide 27 as a white foam. TLC (silica gel n-butanol, H₂O, acetic acid, EtOAc, 1:1:1:1) Rf=0.1–0.2. MS m/e 517 (M+; tristrimethylsilyl-15). NMR (D₂O); δ1.2–2.2 (10,m); 2.85 (3H,s); 3.1–3.7 (5H,m); 4.0–4.4 (1H,m).

EXAMPLE 23

N-(1-Carboethoxy-3-phenylpropyl)-α-azaglycinyl-(L)-proline-t-butyl ester (28)

Using the procedure described in Example 10 above for 14, carbazide 3 (0.458 g; 2.00 mmol) and ethyl 4-phenyl-2-butanoate (0.412 g; 2.00 mmol) were used to prepare azapeptide 28, which was purified by flash chromatography on silica gel (0.633 g; 1.51 mmol; 76%). TLC (silica gel, CH₂Cl₂—CH₃OH, 10:1) Rf=0.75. MS m/e 419 (M+) NMR (COCl₃): δ1.22 (3H, t, J=7); 1.37 (9H,s); 1.8–2.3 (6H,m): 2.6–3.0 (2H,m); 3.2–3.8 (3H,m); 4.0–4.4 (1H,m); 4.08 (2H, q, J=7); 4.6–4.8 (1H, broad); 6.6 (1H,6s); 7.17 (5H,6s). IR (CHCl₃): 3500–3300, 1730, 1660 cm⁻¹.

EXAMPLE 24

N-(1-Carboethoxy-3-phenylpropyl)-α-azaglycinyl-(L)-proline (29)

Treatment of azapeptide 28 (0.284 g; 0.677 mmol) with trifluoroacetic acid (as described in Example 11) and purification on DOWEX® 50W-X4 (8 g) with H₂O-pyr (50:1) as eluant, gave after freeze-drying, pure azapeptide 29 (0.196 g; 0.541 mmol, 80%) as a white foam. TLC (silica gel, EPAW, 20:5:1:1) Rf=0.5. MS m/e 507 (M+, disilyl). NMR (CDCl₃): δ1.22 (3H, t, J=7); 1.7–2.4 (6H,m); 2.5–3.0 (2H,m); 3.1–3.9 (3H,m); 4.0–4.6 (1H,m); 4.08 (2H,q,J=7); 7.18 (5H,bs); 8.4–9.0 (2H,broad). IR (CHCl₃): 3600–2500; 1780 (shoulder); 1730; 1670, 1610 cm⁻¹.

EXAMPLE 25

N-(1-Carboxy-3-phenylpropyl)-α-azaglycinyl-(L)-proline (30)

To a solution of azapeptide 29 (0.132 g; 0.362 mmol) in ethanol (1.5 ml) was added in sodium hydroxide solution (0.80 ml; 0.80 mmol). The mixture was stirred for 24 hours and then placed onto a column of DOWEX® 50W-X4 (6 g). Elution with H₂O-pyr (50:1) gave, after freeze-drying, pure azapeptide 30 (0.080 g; 0.239 mmol; 66%) as a white powder. TLC (silica gel, EPAW, 10:5:1:3) Rf=0.45. MS m/e 551 (M+, trisilyl). NMR (CDCl₃): δ1.7–2.4 (6H,m); 2.7–3.1 (2H,m); 3.3–4.2 (4H,m); 7.1–7.3 (5H,bs); 8.4–9.4 (2H, broad). IR (CHCl₃): 3600–2500; 1780 (shoulder); 1730, 1670 cm⁻¹.

EXAMPLE 26

Ethyl-4-phenyl-2-oxobutanoate (α-azaglycinyl-(L)-proline t-butyl ester) carbazone (31)

A solution of carbazide 3 (0.458 g; 2.00 mmol) and ethyl 4-phenyl-2-oxobutanoate (0.412 g; 2.00 mmol) in THF (3 ml) was stirred overnight. The resulting carbazone was purified by flash chromatography on silica gel in CH₂Cl₂—CH₃OH (100:1), giving 0.515 g (1.23 mmol; 62%) of 31 as a colorless oil. TLC (silica gel; CH₂Cl₂—CH₃OH, 20:1) Rf=0.2–0.4. MS m/e 417 (M+). IR (CHCl₃): 1740, 1720, 1660, 1610 cm⁻¹. Analysis: Calculated for C₂₂H₃₁N₃O₅: C, 63.29; H, 7.48; N, 10.06. Found: C, 63.69; H, 7.66; N, 10.02. NMR (CDCl₃): δ1.25 (3H, t, J=7); 1.37 (9H, S); 1.7–2.1 (4H,m); 2.7–2.9 (4H,bs); 3.4–3.7 (2 H,m); 4.13 (2H, q, J=7); 4.5–4.7 (1 H,m); 7.2–7.4 (5H, bs).

EXAMPLE 27

Ethyl-4-phenyl-α-oxobutanoate
(α-azaglycinyl-(L)-proline) carbazone (32)

A solution of carbazone 31 (80.0 mg; 0.192 mmol) in trifluoroacetic acid (3 ml) was allowed to stand for 2 hours. Removal of solvent gave a light-brown solid, which was recrystallized from hexanes-ethanol (2:1), giving pure carbazone 32 (31 mg; 0.085 mmol; 44%), mp 126°–127°. TLC (silica gel, EPAW, 20:5:1:1) Rf=0.5. Analysis: Calculated for $C_{18}H_{23}N_3O_5$: C, 59.82; H, 6.41; N, 11.63. Found: C, 59.66; H, 6.44; N, 11.48. MS m/e 361 (M+). NMR (CDCl$_3$): δ1.32 (3H, t, J=7); 1.9–2.4 (4H,m); 2.80 (4H, bs); 3.4–3.8 (2H,m); 4.23 (2H, q, J=7); 4.5–4.8 (1H, m); 7.13 (5H,s). IR (CHCl$_3$): 3600–2500; 1760; 1740 (shoulder); 1670; 1630; 1580 cm$^{-1}$.

EXAMPLE 28

N-(1-Carboethoxy-3-phenylpropyl)-α-azaphenyl alanyl-(L)-proline t-butyl ester (34)

A solution of carbazide 12 (0.568 g; 1.78 mmol) and ethyl 4-phenyl-2-oxobutanoate (0.367 g; 1.78 mmol) in absolute ethanol (2 ml) containing glacial acetic acid (3 drops) was heated at reflux for 4 hours. The resulting carbazone 33 was purified by flash chromatography on silica gel in CH$_2$Cl$_2$—CH$_3$OH (100:1), giving pure material (0.387 g; 0.763 mmol); 43%) as a colorless oil. TLC (silica gel, CH$_2$Cl$_2$—CH$_3$OH, 20:1) Rf=0.7. MS m/e 507 (M+). NMR (CDCl$_3$): δ1.32 (3H, t, J=7); 1.40 (9H,s); 1.7–2.2 (4H, m); 2.68 (4H,s); 3.4–3.8 (2H,m); 4.22 (2H, q, J=7); 4.5–4.8 (1H,m); 4.93 (2H,s); 6.8–7.3 (5H,m); 7.13 (5H,s). IR (CHCl$_3$), 3000, 1730, 1660, 1600 cm$^{-1}$.

The carbazone 33 (0.387 g; 0.763 mmol) was treated for 24 hours with sodium cyanoborohydride (0.032 g; 0.509 mmol) in absolute ethanol (3 ml). Workup as described in Example 10 gave azapeptide 34 as a colorless oil. Flash chromatography on silica gel in CH$_2$Cl$_2$—CH$_3$OH (100:1) gave pure azapeptide (0.293 g, 0.575 mmol; 75%), TLC (silica gel, CH$_2$Cl$_2$—CH$_3$OH, 20:1) Rf=0.60, 0.65, (2 diastereomers, 1:1). IR (CHCl$_3$): 1740, 1630 cm$^{-1}$. MS m/e 509 (M+). NMR (CDCl$_3$): δ1.22 (3H, t, J=7); 1.42 (9H,s); 1.7–2.2 (6H,m); 2.4–2.8 (2H,m); 3.4–3.8 (2H,m); 4.03 (2H, q, J=7); 4.4–4.7 (3H,m); 7.22 (5H, bs); 7.32 (5H,bs).

EXAMPLE 29

N-(1-Carboethoxy-3-phenylpropyl)-α-azaphenylalanyl-(L)-proline (35)

A solution of azapeptide 34 (0.293 g; 0.575 mmol) in trifluoroacetic acid (6 ml) was allowed to stand for 2 hours. The solution was evaporated to dryness, and the light brown residue was dissolved in ether (25 ml). The solution was washed several times with brine, dried (MgSO$_4$) and evaporated, giving 35 as white foam (0.193 g; 0.427 mmol; 74%). TLC (silica gel; EPAW: 20:5:1:1) Rf=0.75. MS m/e 525 (M+, monotrimethylsilyl). NMR (CDCl$_3$): δ1.22 (3H, t, J=7); 1.7–2.3 (6H,m); 2.4–2.7 (2H,m); 3.4–3.8 (3H,m); 4.05 (2H, q, J=7); 4.1–4.4 (1H,m); 4.52 (2H,bs); 7.0–7.6 (10H,m). IR (CHCl$_3$); 3600–2500; 1740; 1680 cm$^{-1}$.

EXAMPLE 30

N-(1-Carboxy-3-phenylpropyl)-α-azaphenyl-alanyl-(L)-proline (36)

To a solution of azapeptide 35 (0.140 g; 0.309 mmol) in absolute ethanol (1.5 ml) was added aqueous sodium hydroxide solution (0.70 ml; 0.70 mmol). Stirring was continued for 24 hours. The reaction mixture was placed onto a column of DOWEX® 50W-X4 (6 g). Elution with H$_2$O and then H$_2$O-pyr (50:1) gave after freeze-drying, pure azapeptide 36 (0.0626 g; 0.147 mmol; 48%) as a white powder. TLC (silica gel; EPAW, 10:5:1:3) Rf=0.80, 0.85 (2 diastereomers). MS m/e 569 (M+, bistrimethylsilyl). NMR (CDCl$_3$): δ1.6–2.2 (6H,m); 2.4–2.8 (2H,m); 3.5–3.9 (3H,m); 4.3–4.7 (3H,m); 7.1–7.5 (10H,m). IR (CHCl$_3$): 3500–2900, 1730, 1650 cm$^{-1}$.

EXAMPLE 31

N-(1-Carbobenzyloxy-3-phenylpropyl)-α-azavalinyl-(L)-proline t-butyl ester (37)

A solution of carbazide 36 (0.271 g; 1.00 mmol) and benzyl 4-phenyl-2-oxobutanoate (0.295 g; 1.10 mmol) in THF (3 ml) containing glacial acetic acid (2 drops) was warmed at reflux for 8 hours. TLC (silica gel; hexanes-EtAc, 2:1) showed product carbazones at Rf=0.50, 0.55. MS m/e 521 (M+). The residue after evaporation was dissolved in ethanol and treated with sodium cyanoborohydride (63 mg; 1.00 mmol). After 4 hours, workup as described in Example 10 gave the product, which was purified by chromatography on silica gel (Baker 1.5×20 cm) in hexanes-EtOAc (10:1). TLC of the pure azapeptide (0.307 g; 0.587 mmol; 59%) on silica gel (hexanes-EtAc; 5:1) showed 2 diastereomers at Rf=0.30, 0.35 (1:1 mixture). MS m/e 523 (M+). NMR (CDCl$_3$): δ1.28, 1.30 (6H, pair of triplets, J=6); 1.42 (9H,s); 1.8–2.4 (6H,m); 2.6–3.0 (2H,m); 3.4–3.7 (4H,m); 4.3–4.7 (1H,m); 5.1–5.3 (2H,m); 7.17 (5H, bs); 7.33 (5H,s). IR (CHCl$_3$): 3000; 1740; 1650 cm$^{-1}$.

EXAMPLE 32

1-(Carboxy-3-phenylpropropyl)-α-azavalinyl-(L)-proline (39)

A solution of azapeptide diester 37 (0.105 g; 0.201 mmol) in trifluoroacetic acid (4 ml) was allowed to stand for 2 hours. Solvent was evaporated, and a solution of the residue in ethyl acetate (25 ml) was washed several times with H$_2$O and then dried (MgSO$_4$). The residue on evaporation (0.100 g) showed a single spot by TLC (silica gel; EPAW; 20:5:1:1) Rf=0.7. MS m/e 539 (M+, monotrimethylsilyl). The crude azapeptide (38) was dissolved in ethyl acetate (3 ml) and glacial acetic acid (1 ml) and hydrogenated for 2 hours with 10% Pd/C (100 mg). Filtration of the catalyst and evaporation of solvent gave a white foam which was purified by chromatography on a column of LH-20 (in CH$_3$OH). The resulting azapeptide 39 (colorless oil) (52 mg; 0.138 mmol; 69%) showed a single spot on TLC (silica gel; EPAW, 20:5:1:1). MS m/e 521 (M+, bistrimethylsilyl). NMR (CDCl$_3$): δ1.0–1.4 (6H,m): 1.8–2.4 (6H,m); 2.6–3.0 (2H,m); 3.2–3.8 (4H,m); 4.2–4.6 (1H,m); 7.1–7.3 (5H, 6s). IR (CHCl$_3$): 3600–2500; 1730; 1640 cm$^{-1}$.

EXAMPLE 33

N$^\alpha$-(1-Carbobenzyloxy-3-phenylpropyl)-N$^\delta$-t-Boc-α-azalysinyl-(L)-proline t-butyl ester (41)

Carbazide 10 (0.308 g; 0.779 mmol) and benzyl 4-phenyl-2-oxobutanoate (0.230 g; 0.866 mmol) were combined with dry tetrahydrofuran (2.5 ml) and the solution was heated at reflux for 4 hours. The product was filtered through silica gel (Baker, 1.5×20 cm) in hexane-ethyl acetate (2:1), this process permitting separation of excess α-ketoester as a forerun. The resulting product (0.274 g) was a mixture of carbazone isomers (40) by TLC (silica gel; hexanes-EtOAc (2:1) Rf=0.3 and 0.5. This was dissolved in ethanol (2 ml) and treated with sodium cyanoborohydride (27 mg; 0.52 mmol). After 4 hours, the reaction mixture was treated as described in Example 10 giving crude product as a colorless oil. Purification on silica gel (Baker; 1.5×20 cm) in hexanes-EtOAc (5:1) gave azapeptide 41 (0.181 g; 0.279 mmol; 36%) as a 1:1 mixture of diastereomers. TLC (silica gel; hexanes-EtOAc, 2:1; 2 developments) Rf=0.25, 0.30. MS m/e 652 (M+) NMR (CDCl$_3$): δ1.42 (18H,s); 1.7–2.8 (12H,m); 3.0–3.5 (6H,m); 4.2–4.6 (2H,m); 4.8–5.0 (1H, broad); 5.08, 5.12 (2H,2S); 7.1–7.2 (5H,bs); 7.25 (5H,s).

EXAMPLE 34

N$^\alpha$-(1-Carbobenzyloxy-3-phenylpropyl)-α-azalysyl-(L)-proline (42)

A solution of azapeptide ester 41 (0.181 g; 0.279 mmol) in trifluoroacetic acid (4 ml) was allowed to stand for 4 hours at room temperature. The mixture was evaporated to dryness, and the resulting light brown residue was purified by chromatography on 50W-X4 resin (10 g). Elution with H$_2$O-pyridine (50:1) gave pure azapeptide 42 (84.3 mg, 0.170 mmol; 61%) as a white foam. TLC (silica gel; EPAW 10:5:1:3) Rf=0.5. NMR (DMSO-d$_6$; 300 MHz)=1.4–2.0 (10H,m); 2.5–2.9 (2H,m); 3.1–3.7(7H,m); 4.0–4.1 (1H,m); 5.09, 5.11 (2H, 2 x S); 7.1–7.3 (5H,m); 7.40 (5H,s). IR (CHCl$_3$): 3600–2500, 1730, 1630 cm$^{-1}$.

EXAMPLE 35

N$^\alpha$-(1-Carboxy-3-phenylpropyl)-α-azalysyl-(L)-proline (43)

Azapeptide 42 (34.3 mg; 0.069 mmol) was combined with ethyl acetate (1.5 ml) and acetic acid (0.5 ml) and the resulting solution was exposed to 1 atm. of hydrogen, using 10% Pd(C) (50 mg) as catalyst. After 4 hours, the catalyst was removed by filtration, and the resulting product (14.5 mg) was purified by chromatography on a column of LH-20 (in methanol). The product 43 (9.4 mg; 0.023 mmol; 33%) showed a single spot on TLC (silica gel; EPAW 10:5:1:3) Rf=0.35. NMR (DMSO-d6)=1.6–2.0(10H, m); 2.4–2.6 (2H, m); 2.8 (2H, bs); 3.0–3.5 (6H, m); 4.4 (1H, bs); 7.1–7.3 (5H, m).

EXAMPLE 36

N$^\alpha$-(1-Carbobenzyloxy-5-phthalimidopentyl)-N$^\delta$-t-Boc-α-azalysyl-(L)-proline-t-butyl ester Using the procedure described for azapeptide 14 in Example 10, carbazide 10 (0.142 g; 0.356 mmol) and benzyl 6-phthalimido-2-hexanoate (0.130 g; 0.356 mmol) were used to prepare azapeptide 44 in 50% yield (0.133 mg; 0.177 mmol) after flash chromatography on silica gel (1.5×22 cm; hexanes-EtAc, 1:1). TLC (silica gel, hexanes-EtAc, 1:1; 2 developments) showed 2 diastereomers, Rf 0.45, 0.50 (1:1). MS m/e 749 (M+). IR (CHCl$_3$): 1775, 1730 (shoulder), 1710, 1645 cm$^{-1}$. NMR (CDCl$_3$): δ1.42 (18H,s); 1.3–2.2 (14H,m); 3.0–3.8 (9H,m); 4.3–4.5 (2H, broad); 5.10, 5.13 (2H, 2 x S); 7.27 (5H,s); 7.7–7.9 (4H,m).

EXAMPLE 37

N$^\alpha$-(1-Carboxyl-5-phthalimidopentyl)-N$^\delta$-t-Boc-α-azalysyl-(L)-proline-t-butyl ester (45)

A solution of azapeptide 44 in ethyl acetate (3 ml) containing 3 drops of glacial acetic acid was hydrogenated at 1 atm. for 18 hours with 10% Pd(C) (60 mg). The resulting azapeptide 45 (89.2 mg; 0.135 mmol; 94%) was purified by TLC (silica gel; EPAW; 20:5:1:1) Rf=0.75. MS m/e 803 (M+, bistrimethylsilyl). NMR (CDCl$_3$); δ1.43 (18H,m); 1.4–2.0 (14H,m); 3.0–3.8 (9H,m); 4.3–4.5 (1H,m); 5.0–5.3 (1H, broad); 7.2–7.4 (1H, broad); 7.7–7.9 (4H,m).

EXAMPLE 38

N$^\alpha$-(1-Carboxy-5-phthalidimidopentyl)-α-azalysyl-(L)-proline (46)

A solution of azapeptide 45 (89.2 mg; 0.135 mmol) in trifluoroacetic acid (3 ml) was allowed to stand for 2 hours. Solvent was removed, and the light-brown residue was chromatographed on DOWEX® 50W-X4 (7.5 g). Elution with H$_2$O-pyr (50:1) gave pure azapeptide 46 (61.6 mg; 0.122 mmol; 91%) as a white foam. TLC (silica gel; EPAW, 10:5:1:3) Rf=0.25. NMR (CD$_3$OD); δ1.3–2.2 (14H,m); 2.9–3.1 (2H,m); 3.4–3.8 (7H,m); 4.3–4.6 (1H,m); 7.80 (4H,s).

EXAMPLE 39

N$^\alpha$-(5-Amino-1-carboxypentyl)-α-azalysyl-(L)-proline (47)

To a solution of azapeptide 46 (55.6 mg; 0.110 mmol) in methanol (1 ml) was added anhydrous hydrazine (12 mg, 0.378 mmol). The solution was stirred for 18 hours and then filtered to remove the white precipitate. The residue, after evaporation, was chromatographed on DOWEX® 50W-X4 (8 g), using H$_2$O-pyr (50:1) as eluant. The product (47) (35.9 mg, 0.0923 mmol; 84%) was a white powder. TLC (silica gel; H$_2$O—BuOH—AcOH,1:1:1) Rf=0.2, 0.4. MS m/e 661 (tetratrimethylsilyl). NMR (DMSO-d6)=1.3–1.8 (12H, m); 2.6–2.8(2H,m); 3.0–3.6 (8 H,m).

EXAMPLE 40

N-(α-Azaalanyl)-(L)-1,2,3,4-tetrahydro-3-isoquinolinecarboxylic acid t-butyl ester (48)

(L)-1,2,3,4-Tetrahydro-3-isoquinolinecarboxylic acid, [prepared by the procedure of Yamada and Kunieda *Chem. Pharm. Bull.*, 15, 490–8 (1967)] is converted to the corresponding t-butyl ester using the procedure of Taschner, et. al. [*Liebigs. Ann. Chem.*, 646, 134–6 (1961)]. A solution of the ester and one equivalent of triethylamine in methylene chloride is added to a slight excess of phosgene (12.5% solution in benzene). The resulting mixture is filtered and evaporated and the resulting residue is dissolved in methylene chloride and added with ice cooling to a solution of methylhydrazine (1 equiv.) and triethylamine (1 equiv.) in methylene chloride. The mixture is stirred for several hours, then filtered and evaporated. The resulting crude product is purified by chromatography on silica gel using methylene chloride-methanol mixtures as eluant.

EXAMPLE 41

N-[N-(1-Carboethoxy-3-phenylpropyl)-α-azaalanyl]-(L)-1,2,3,4-tetrahydro-3-isoquinolinecarboxylic acid t-butyl ester (49)

Using the procedure described in Example 10, carbazide (48) and ethyl 4-phenyl-2-oxobutanoate are used to prepare azapeptide (49), which is purified by chromatography on silica gel with methylene chloride-methanol mixtures as eluant.

EXAMPLE 42

N-[N-(1-Carboethoxy-3-phenylpropyl)-α-azaalanyl]-(L)-1,2,3,4-tetrahydro-3-isoquinolinecarboxylic acid (50)

A solution of azapeptide (49) in trifluoroacetic acid is allowed to stand for 4 hours at room temperature. Solvent is removed and the residue is chromatographed on DOWEX® 50W-X4 resin, using $H_2O$-pyr (50:1) as eluant, providing the product, after freeze-drying, as a white foam.

EXAMPLE 43

N-[N-(1-Carboxy-3-phenylpropyl)-α-azaalanyl]-L-1,2,3,4-tetrahydro-3-isoquinolinecarboxylic acid (51)

A solution of azapeptide (50) in $H_2O$—$CH_3OH$ (1:1) is treated with sodium hydroxide (2.5 equivalents) for 24 hours. The mixture is placed onto a column of DOWEX® 50W-X4. Elution with $H_2O$-pyr (50:1) gives the product, after freeze-drying, as a white foam.

EXAMPLE 44

$N^α$-(1-Carboethoxy-3-phenylpropyl)-$N^δ$-t-Boc-α-azalysyl-(L)-proline t-butyl ester (52R, 52S)

A solution of carbazide 10 (0.593 g; 1.48 mmol) and ethyl 4-phenyl-2-oxobutanoate (0.336 g; 1.63 mmol) in dry THF (7.5 ml) was heated at reflux for 16 hours. The solvent was removed by evaporation and absolute ethanol (5 ml) and sodium cyanoborohydride (93 mg; 1.48 mmol) were added. The solution was stirred for 4 hours, then treated as described in Example 10, giving the crude product as a colorless oil. TLC (silica gel; 1:1 hexanes-EtOAc) showed a mixture (1:1) of diastereomers, Rf-0.25, 0.30. Purification by column chromatography on silica gel (1:1 hexanes-EtOAc) (yield=0.755 g; 1.28 mmol; 87%), followed by careful separation of the diastereomers on silica gel (2:1 hexanes-EtOAc) provided the following:

(1) 52S More mobile diastereomer (184 mg). MS: m/e 591 (M+ +1) Analysis: Calculated for $C_{31}H_{50}N_4O_7$: C, 63.02; H, 8.53; N, 9.49. Found: C, 63.17; H, 8.60; N, 9.12. NMR (CDCl₃); δ 1.28 (3H, t, J=6); 1.43 (9H, S); 1.48 (9H, S); 1.6–2.1 (10H, m); 2.2–2.3 (2H, m); 2.67 (2H, t, J=8); 3.0–3.5 (7H, m); 4.17 (2H, q, J=7); 4.22 (1H, t, J=7); 4.94 (1H, broad S); 5.05 (1H, broad S); 7.1–7.3 (5H, m).

(2) Mixed fractions (70 mg).

(3) 52R; Less mobile diastereomer (327 mg). MS: m/e 591 (M+ +1) Analysis: Found: C, 62.59; H, 8.53; N, 9.21. NMR (CDCl₃); δ1.28 (3H, t, J=7); 1.46 (18H, S); 1.6–2.1 (10H, m); 2.2–2.3 (2H, m); 2.6–2.8 (2H, m); 3.1–3.3 (4H, m); 3.4–3.5 (3H, m); 4.17 (2H, q, J=7); 4.40 (1H, t, J=7); 4.9–5.0 (1H, broad); 7.2–7.4 (5H, m).

EXAMPLE 45

N-(1-Carboethoxy-3-phenylpropyl)-α-azalysyl-(L)-proline dihydrochloride (53R, 53S)

A solution of 52S (more-mobile diastereomer; 108 mg) in ice-cold concentrated hydrochloric acid (6 ml) was stirred for 18 hours at 5° C. The solution was diluted with $H_2O$ (25 ml) and evaporated giving 53S as a white solid. (89 mg) TLC (silica gel; 70:30:6:4 $CHCl_3$:$CH_3OH$:$H_2O$:HOAc) Rf=0.5. NMR (D₂O):=1.18 (3H, t, J=7); 1.5–2.0 (10H, m); 2.1–2.3 (2H, m); 2.5–2.7 (2H, m); 2.9–3.1 (2H, m); 3.1–3.6 (5H, m); 4.09 (2H, q, J=7); 4.3–4.4 (1H, m); 7.1–7.3 (5H, m). Starting from 52R (less-mobile diastereomer; 111 mg) there was obtained, by the same procedure, 53R (90 mg) as a white solid. TLC (silica gel; 70:30:6:4 $CHCl_3$:$CH_3OH$:$H_2O$:HOAc) Rf=0.5. NMR (D₂O): 1.24 (3H, t, J=7); 1.5–2.1 (10H, m); 2.2–2.4 (2H, m); 2.6–2.8 (2H, m); 2.9–3.1 (2H, m); 3.2–3.7 (5H, m); 4.12 (2H, q, J=7); 4.6–4.7 (1H, m); 7.2–7.4 (5H, m).

EXAMPLE 46

N-(1-Carboxy-3-phenylpropyl)-α-azalysyl-(L)-proline dihydrochloride (54R, 54S)

A solution of 53S (89 mg) in aqueous sodium hydroxide solution (0.25 N; 3 ml) was stirred for 18 hours, then neutralized by addition of hydrochloric acid (0.50 N). The product was freeze-dried, then purified by ion-exchange on DOWEX 50W-X4. Elution with 25:1 $H_2O$:pyr and freeze-drying provided 54S (free base) (65 mg; 0.16 mmol; 87%) as a white foam. This was further purified by chromatography on silica gel (70:30:6:4 $CHCl_3$:$CH_3OH$:$H_2O$:HOAc) and reconcentrated from hydrochloric acid (6N; 5 ml), giving 54S (5 mg) as the dihydrochloride salt. TLC (silica gel, 70:30:6:4. CMWA) Rf=0.35. Analysis: Calculated for $C_{20}H_{28}N_4O_5$.2HCl.7/2 $H_2O$: C, 44.44; H, 6.90; N, 10.37. Found: C, 44.44; H, 6.78; N, 10.15. NMR (D₂O): 1.5–2.1 (10H, m); 2.2–2.4 (2H, m); 2.6–2.8 (2H, m); 2.9–3.1 (2H, m); 3.3–3.6 (5H, m); 4.3–4.45 (1H, m); 7.2–7.4 (5H, m). Starting from 53R (90 mg), there was obtained, using the same procedure, 54R (54 mg) as the dihydrochloride salt. NMR (D₂O): 1.5–2.1 (10H, m); 2.1–2.3 (2H, m); 2.6–2.8 (2H, m); 3.2–3.7 (5H, m); 4.4–4.45 (1H, m); 7.2–7.4 (5H, m). TLC (silica gel: 70:30:6:4 CMWA) Rf=0.35.

EXAMPLE 47

N-(1-Carboethoxy-3-phenylpropyl)-α-azaalanyl-(L)-prolin e ethyl ester hydrochloride (55)

An ice-cold solution of N-(1-carboethoxy-3-phenylpropyl)-α-azaalanyl-(L)-proline t-butyl ester (16S) in absolute ethanol was saturated with hydrogen chloride. After one hour, the solution was evaporated to dryness and the product purified by chromatography on LH-20 (in methanol).

EXAMPLE 48

Ethyl 4-phenyl-2-hydrazinobutanoate trifluoroacetate (56)

A solution of ethyl 4-phenyl-2-oxobutanoate (2.06 g; 10 mmol) and t-butylcarbazate (1.32 g; 10 mmol) in THF (50 ml) can be warmed at reflux for 8 hours. Solvent can be evaporated and the residue taken up in anhydrous ethanol (25 ml). Sodium cyanoborohydride (0.31 g; 5 mmol) can be added, and the solution stirred for 4 hrs. The residue, after evaporation, can be stirred with EtOAc (50 ml) and hydrochloric acid (0.5 N: 20 ml) for 30 minutes. The aqueous layer can be neutralized by addition of $K_2CO_3$ and extracted with EtOAc (3×25 ml). The combined organic portions can be washed with $H_2O$ and brine and dried ($MgSO_4$). The residue, upon evaporation, can be purified by chromatography on silica gel, affording N-(1-carboethoxy-3-phenylpropyl)-N'-BOC-hydrazine. An ice-cold solution of the above hydrazine in trifluoroacetic acid can be allowed to stand for 1 hr. Removal of solvent can provide hydrazine (56) as the trifluoroacetic acid salt.

EXAMPLE 49

(4R)-4-Carboethoxy-2-(2-hydroxyphenyl)thiazolidine (57)

The procedure of M. Schubert (*J. Biol. Chem.*, 114, 341 (1936)) was used to prepare 57 starting from L-cysteine ethyl ester and salicylaldehyde. Purification by silica gel chromatography afforded 57 as a thick oil. TLC (silica gel; 3:1 cyclohexane-EtOAc) showed a mixture of 2 isomers, Rf=0.4, 0.5. IR (film): 3300 (sharp), 3000, 1740, 1430 cm$^{-1}$. NMR ($CCl_4$): 1.28 (3H, t, J=7); 2.9–3.5 (2H, m); 3.8–4.4 (3H, m); 5.50, 5.80 (1H, 2x broad s); 6.5–7.3 (4H, m).

EXAMPLE 50

N-[N-(1-Carboxy-3-phenylpropyl)-α-azaglycinyl]-4(R)carboethoxy-2-(2-hydroxyphenyl)thiazolidine (58)

An ice-cold solution of phosgene (1.1 M solution in toluene; 0.91 ml) was diluted with $CH_2Cl_2$ (3 ml) and then a solution of 56 (0.34 g, 1.0 mmol) and triethylamine (0.28 ml; 2.0 mmol) in $CH_2Cl_2$ (3 ml) was added slowly with cooling (ice-bath). Then a solution of 57 (0.25 g; 1.0 mmol) and triethyl amine (0.14 ml; 1.0 mmol) in $CH_2Cl_2$ (3 ml) was added and stirring was continued at room temperature for 6 hours. The reaction mixture was diluted with EtAc (25 ml) and extracted with $H_2O$ (2×10 ml) and brine, and dried ($MgSO_4$). The residue after evaporation was subjected to chromatography on silica gel, allowing isolation of 58.

EXAMPLE 51

N-[(1-Carboxy-3-phenylpropyl)-α-azaglycyl]-4(R)-carboxy-2-(2-hydroxyphenyl)thiazolidine (59)

The above diester (Example 50) can be dissolved in aqueous sodium hydroxide (2N; 5 ml) and stirred for 1 hr. The resulting solution can be acidified with dilute hydrochloric acid and the product (59) isolated by ion-exchange chromatography on DOWEX 50W-X4 resin.

EXAMPLE 52

Improved Procedure for:
N-t-BOC-4-Aminobutyraldehyde carbobenzoxyhydrazone (7)

A solution of 4-aminobutyraldehyde diethyl acetal (9.33 g) and di-t-butyldicarbonate (13.3 g) in chloroform (120 ml) was allowed to stir for 2 hrs. The mixture was concentrated and to the residue were added THF (110 ml) and hydrochloric acid (0.5 N; 120 ml). The mixture was stirred vigorously for 1 hr, then cooled in an ice-bath and diluted with ether (100 ml). Sodium hydroxide solution (1 N) was added until the aqueous layer was slightly basic (pH=8). The layers were separated and the aqueous layer extracted with ether (3×100 ml). The combined ether positions were washed with $H_2O$ and brine, and dried ($K_2CO_3$). Evaporation gave crude N-t-BOC-2-pyrrolidinol (6) as a colorless oil (20 g). This material was combined with carbobenzoyhydrazine (6.64 g) and THF (60 ml). The resulting solution was warmed at reflux for 3 hours, then allowed to stir for 20 hours at room temperature. Evaporation of solvent and recrystallization of the resulting solid from hexanes-EtOc gave 7 (8.4 g; 43%), m.p. 99°–104° C. TLC (silica gel; EtOAc) showed a mixture (1:1) of isomers, Rf=0.50, 0.55. Analysis: Calculated for $C_{17}H_{26}N_3O_4$: C, 60.70; H, 7.79; N, 12.49; Found: C, 61.09; H, 7.69; N, 12.45. NMR ($CDCl_3$): δ1.43, 1.47 (9H, 2xs); 1.8–2.1 (2H, m); 2.2–2.5 (1H, m); 3.0–3.5 (3H, m); 4.8–5.0 (1H, m); 5.18, 5.27 (2H, 2xs); 7.3 (5H, s).

EXAMPLE 53

N-(t-Boc-4-aminobutyl)-N'-CBZ-hydrazine (8)

To a solution of carbazone 7 (6.0 g) in THF (35 ml) and ethanol (20 ml) was added sodium cyanoborohydride (1.1 g). The mixture was cooled (ice-bath) and a soluion of anhydrous HCl in ethanol (a saturated soluion diluted 4 times with ethanol) was added slowly. After 6 ml had been added, TLC showed no carbazone remaining. The mixture was concentrated and then diluted with EtOAc (125 ml) and aqueous hydrochloric acid (0.5 N; 30 ml). The mixture was stirred vigorously for 15 minutes and then the aqueous layer was neutralized by addition of $K_2CO_3$ and extracted with EtOAc (3×50 ml). The combined organic portions were washed with $H_2O$ and brine and dried ($MgSO_4$) The residue after evaporation was purified by column chromatography on silica gel and then recrystallized from hexanes-EtOAc, giving 8 (2.7 g; 8.2 mmol; 46%) m.p. 73°–74° C.

EXAMPLE 54

N-t-BOC-α-azalysyl-L-proline-t-butyl ester (10)

A solution of carbazide 8 (1.50 g; 4.45 mmol) and carbamoyl chloride (prepared as described in Example 1; 6.7 mmol, crude) in dry THF (7.5 ml) containing triethylamine (0.66 ml; 4.50 mmol) was warmed at reflux for 8 hrs. The residue, after evaporation was slurried in EtOAc and filtered. Purification by column chromatography on silica gel (hexanes-EtOAc) gave N$^α$-CBZ-N$^δ$-t-BOC-α-azalysyl-(L)-proline-t-butyl ester (2.29 g, 4.29 mmol; 96%) as a colorless oil. TLC (silica gel, 1:1 hexanes-EtOAc) Rf=0.35. Analysis: Calculated for $C_{27}H_{42}N_4O_7$: C, 60.66; H, 7.92; N, 10.48. Found: C, 61.15; H, 8.33; N, 10.04. NMR ($CDCl_3$); 1.43 (18H, s); 1.5–1.7 (4H, m); 1.75–2.3 (4H, m); 3.1–3.4 (3H, m); 3.4–3.6 (4H, m); 4.3 (1H, broad); 4.8 (1H, broad); 5.22 (2H, broad s); 7.4 (5H, broad s). A solution of this material in absolute ethanol (20 ml) was hydrogenated with 10% pd(C) (100 mg) for 3 hrs (1 atm). Filtration of the catalyst and removal of solvent gave carbazide 10 as a colorless oil. TLC (silica gel, 10:1 $CH_2Cl_2:CH_3OH$) Rf=0.7.

A portion of this material (0.10 g) was purified by silica gel chromatography (10:1 ether:methanol). Analysis: Calculated for $C_{19}H_{36}N_4O_5$: C, 56.97; H, 9.06; N, 13.99. Found: C, 57.00; H, 9.29; N, 14.06.

EXAMPLE 55

Improved procedure for:
N-(1-Carboethoxy-3-phenylpropyl)-α-azaalanyl-(2)-proline (17S)

Azapeptide 16S (0.180 g; 0.416 mmol) was combined with concentrated hydrochloric acid (5 ml) and the resulting solution wa stirred overnight at 5° C. After dilution with H₂O (25 ml), solvent was removed, giving 17S as a light-yellow oil. This was purified by chromatography on silica gel (85:30:5:1) CHCl₃-CH₃OH-H₂O-HOAc), then reconcentrated from dilute hdyrochloric acid, giving the product (as the hydrochloride) as an oil (0.141 g; 0.341 mmol; 82%). TLC (silica gel, 20:5:1:1 EPAW) Rf=0.65.

EXAMPLE 56

N-(1-Carboxy-3-phenylpropyl)-α-azaalanyl-(L)-proline (19S)

A soluion of azapeptide 16S (more mobile diastereomer; (0.335 g; 0.774 mmol) in trifluoroacetic acid (5 ml) was allowed to stand for 3 hours. The reside after evaporation wa combined with sodium hydroxide (1 N; 3 ml) and THF (0.5 ml) and the resulting solution was stirred under nitrogen for 18 hrs. After neutralization with dilute hydrochloric acid, the solution was placed onto a column of DOWEX 50W-X4 ion-exchange resin (5 g). The product wa eluted with 20:1 H₂O-pyr and freeze-dried to a white foam (0.215 g; 0.1=616 mmol; 80%). A portion of this material (0.052 g) was purified by chromatography on silica gel (85:30:5:1 CHCl₃-CH₃OH-H₂O:HOAc), affording pure product (0.031 g). The disodium salt (0.025 g) precipitated from CH₂Cl₂; m.p. 220–225 (dec). TLC (silica gel; 10:5:1:3 EPAW) Rf=0.45. Analysis: Calculated for $C_{17}H_{23}N_3O_5 \cdot 2Na$: C, 51.65; H, 5.82; N, 10.63. Found: C, 51.54; H, 5.79; N, 10.28. MS (for diacid): m/e 403 (monotrimethylsilyl of M⁺-H₂O). NMR (CDCl₃). 1.7–2.3 (6H, m); 2.6–2.8 (2H, m); 3.00 (3H, s); 3.5–3.6 (3H, m); 4.3–4.5 (1H, m); 7.1–7.3 (5H, m); 7.4–8.0 (2H, broad).

EXAMPLE 57

Additional Compounds of Formula I

Using the procedures and intermediates illustrated in the Examples above, it is possible to synthesize additional compounds of Formula I as shown in Table III. These syntheses make use of the t-butyl esters of amino acids of formula

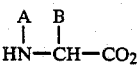

from Table I and known keto acids of esters listed in Table II.

TABLE I

Amino acids of the formula:

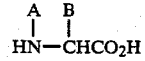

(a) 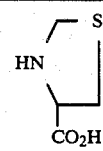

TABLE I-continued

Amino acids of the formula:

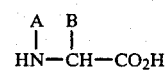

(b) 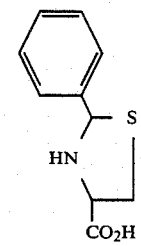

(c) 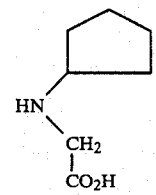

(d) 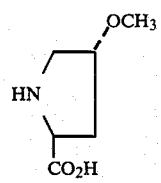

(e) 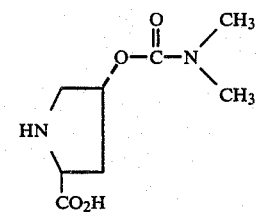

(f) 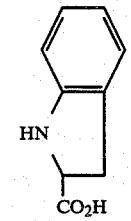

(g) 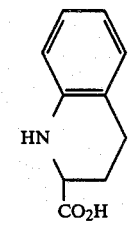

TABLE II

Keto acids and Esters of the Formula:

$$R_1-CO-CO_2R \qquad VI$$

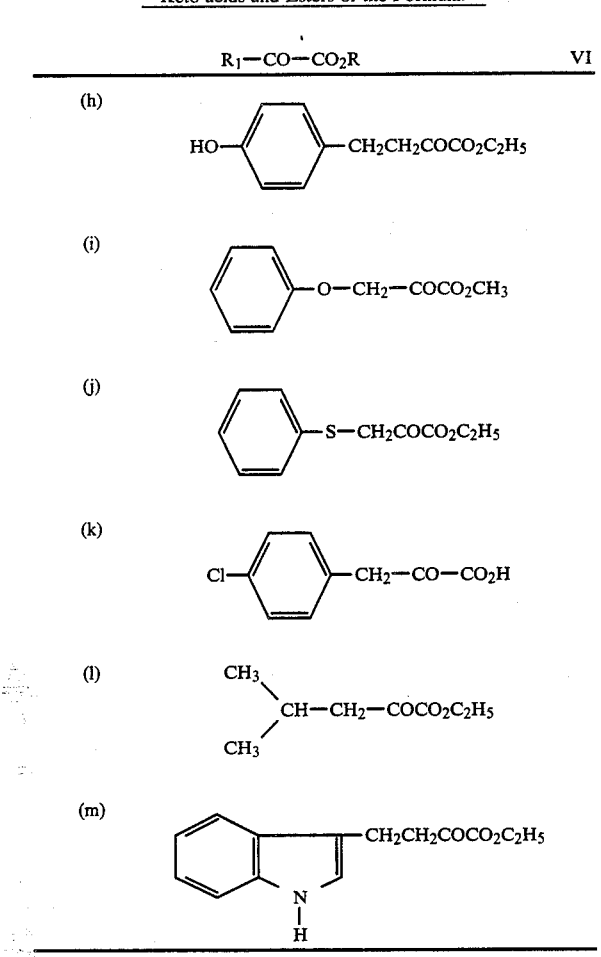

TABLE III

Additional compounds of Formula I:

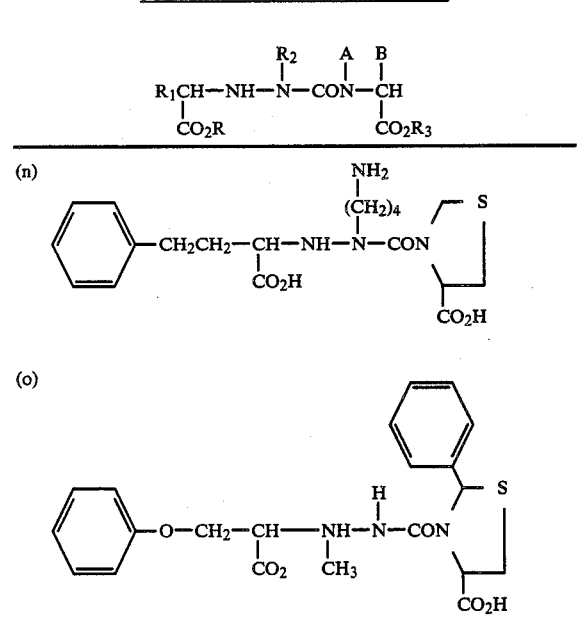

TABLE III-continued

Additional compounds of Formula I:

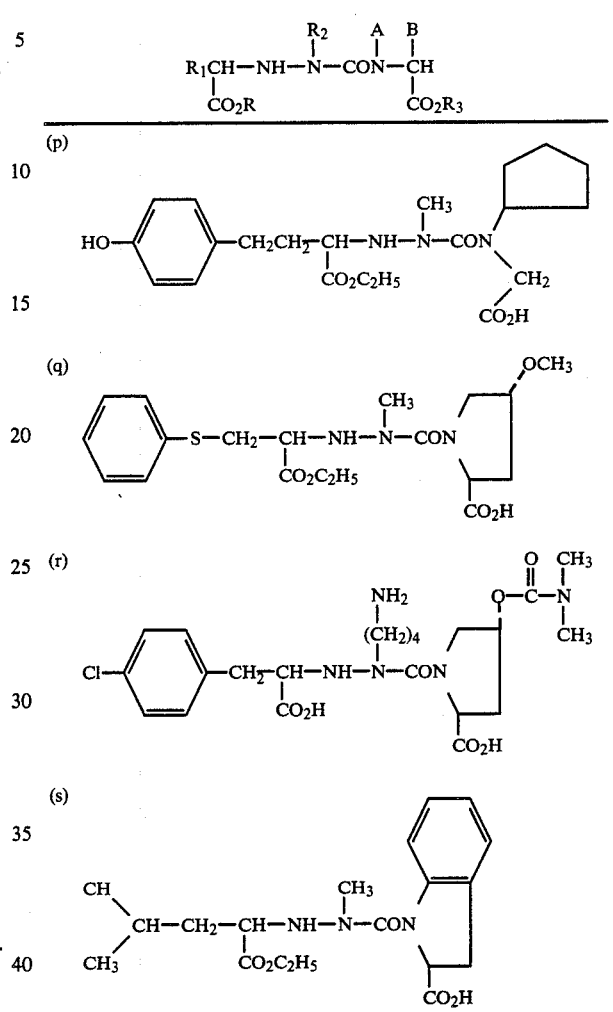

What is claimed:
1. A compound having the formula:

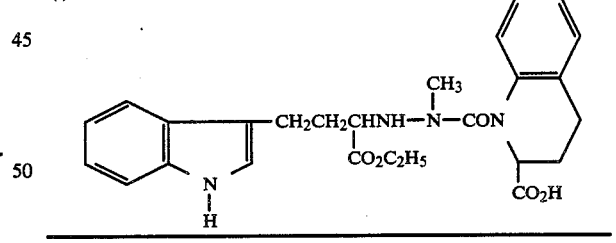

wherein:
R and $R_3$ are independently hydrogen, loweralkyl, loweralkenyl, loweralkynyl, aralkyl;
$R_1$ is aralkyl, and substituted aralkyl wherein the substituents are amino, halo, animoloweralkyl, hydroxy, loweralkoxy, loweralkyl, loweralkenyl, and loweralkynyl; loweralkyl substituted by amino, acylamino, aryloxy, arylthio, and hydroxyl;

$R_2$ is hydrogen, loweralkyl, loweralkenyl, loweralkynyl, amino loweralkyl, amino loweralkenyl, aminoloweralkynyl, aralkyl;

A and B are joined together to form proline and, the pharmaceutically acceptable salts thereof wherein the aralkyl groups have from one to six carbon atoms in the alkyl portion thereof; aryl, is selected from the group consisting of phenyl, naphthyl or biphenyl; and acyl is a loweralknoyl or aroyl group.

2. A compound of claim 1 wherein the asymmetric carbon atoms are in the L-amino acid configuration.

3. A compound of claim 1 which is: N-(1-carboxy-3-phenylpropyl)-α-azaalanyl-L-proline.

4. A compound of claim 1 which is: N-[1(S)-carboxy-3-phenylpropyl)]-α-azaalanyl-L-proline.

5. A compound of claim 1 which is: N-(1-ethoxycarbonyl-3-phenylpropyl]-α-azaalanyl-L-proline.

6. A compound of claim 1 which is: N-[1(S)-carboethoxy-3-phenylpropyl]-α-azaalanyl-L-proline.

7. A compound of claim 1 which is: N-(1-carboethoxy-3-phenylpropyl]-α-azaalanyl-L-proline ethyl ester.

8. A compound of claim 1 which is: N-[1(S)-carboethoxy-3-phenylpropyl]-α-azaalanyl-L-proline ethyl ester.

9. A compound of claim 1 which is: $N^\alpha$-(1-carboxy-3-phenylpropyl)-α-axalysyl-L-proline.

10. A compound of claim 1 which is: $N^\alpha$-[1(S)-carboxy-3-phenylpropyl]-α-azalysyl-L-proline.

11. A pharmaceutical composition useful in the treatment of hypertension comprising a pharmaceutically acceptable carrier and a pharmaceutically effective amount of a compound having the formula:

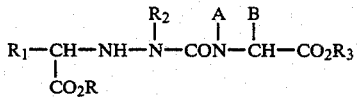

wherein:

R and $R_3$ are independently hydrogen, loweralkyl, loweralkenyl, loweralkynyl, aralkyl;

$R_1$ is aralkyl, and substituted aralkyl wherein the substituents are amino, halo, aminoloweralkyl, hydroxy, loweralkoxy, loweralkyl, loweralkenyl, and loweralkynyl; loweralkyl substituted by amino, acylamino, aryloxy, arylthio, and hydroxyl;

$R_2$ is hydrogen, loweralkyl, loweralkenyl, loweralkynyl, amino loweralkyl, amino loweralkenyl, aminoloweralkynyl, aralkyl;

A and B are joined together to form proline and, the pharmaceutically acceptable salts thereof wherein the aralkyl groups have from one to six carbon atoms in the alkyl portion thereof; aryl, is selected from the group consisting of phenyl, naphthyl or biphenyl; and acyl is a loweralknoyl or aroyl group.

12. The composition of claim 11 wherein said compound is a member of the group:

N-(1-carboxy-3-phenylpropyl)-α-azaalanyl-L-proline;

N-[1(S)-carboxy-3-phenylpropyl]-α-azaalanyl-L-proline;

N-(1-carboethoxy-3-phenylpropyl)-α-azaalanyl-L-proline;

N-[1(S)-carboethoxy-3-phenylpropyl]-α-azaalanyl-L-proline;

N-(1-carboethoxy-3-phenylpropyl)-α-azaalanyl-L-proline ethyl ester;

N-[1(S)-carboxy-3-phenylpropyl)]-α-azaalonyl-L-proline ethyl ester;

$N^\alpha$-(1-carboxy-3-phenylpropyl)-α-azalysl-L-proline; and $N^\alpha$-[1(S)-carboxy-3-phenylpropyl]-α-azalysyl-L-proline.

13. A pharmaceutical composition useful in the treatment of hypertension comprising a pharmaceutically acceptable carrier; a pharmaceutically effective amount of a compound having the formula:

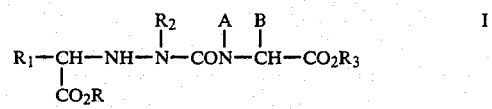

wherein:

R and $R_3$ are independently hydrogen, loweralkyl, loweralkenyl, loweralkynyl, aralkyl;

$R_1$ is aralkyl, and substituted aralkyl wherein the substituents are amino, halo, aminoloweralkyl, hydroxy, loweralkoxy, loweralkyl, loweralkenyl, and loweralkynyl; loweralkyl substituted by amino, acylamino, aryloxy, arylthio, and hydroxyl;

$R_2$ is hydrogen, loweralkyl, loweralkenyl, loweralkynyl, amino loweralkyl, amino loweralkenyl, aminoloweralkynyl, aralkyl;

A and B are joined together to form proline and, the pharmaceutically acceptable salts thereof; wherein the aralkyl groups have from one to six carbon atoms in the alkyl portion thereof; aryl, is selected from the group consisting of phenyl, naphthyl or biphenyl; and acyl is a loweralknoyl or aroyl group and, another antihypertensive and/or diuretic compound selected from the group consisting of hydrochlorothiaxide, timolol, methyl dopa, the pivaloyloxyethyl ester of methyl dopa, indacrinone and variable ratios of its enantiomers, (−)-4-{3-{-[2-(hydroxycyclohexyl)-ethyl]-4-oxo-2-thiaxolidinyl}propyl}benzoic acid, as well a mixtures and combinations thereof.

14. The composition of claim 13 wherein said pharmaceutically effective compound is a member of the group:

N-(1-carboxy-3-phenylpropyl)-α-azaalanyl-L-proline;

N-[1(S)-carboxy-3-phenylpropyl]-α-azaalanyl-L-proline;

N-(1-carboethoxy-3-phenylpropyl)-α-azaalanyl-L-proline;

N-[1(S)-carboethoxy-3-phenylpropyl]-α-azaalanyl-L-proline;

N-(1-carboethoxy-3-phenyipropyl)-α-azaalanyl-L-proline ethyl ester;

N-[1(S)-carboethoxy-3-phenylpropyl]-α-azaalanyl-L-proline ethyl ester;

$N^\alpha$-(1-carboxy-3-phenylpropyl)-α-azalysyl-L-proline; and $N^\alpha$-[1(S)-carboxy-3-phenylpropyl]-α-azalysyl-L-proline.

15. A method of treating hypertension which comprises administering to a patient in need of such treatment a pharmaceutically effective amount of a compound having the formula:

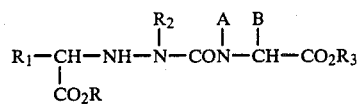

wherein:
R and $R_3$ are independently hydrogen, loweralkyl, loweralkenyl, loweralkynyl, aralkyl;
$R_1$ is aralkyl, and substituted aralkyl wherein the substituents are amino, halo, aminoloweralkyl, hydroxy, loweralkoxy, loweralkyl, loweralkenyl, and loweralkynyl; loweralkyl substituted by amino, acylamino, aryloxy, arylthio, and hydroxyl;
$R_2$ is hydrogen, loweralkyl, lowralkenyl, loweralkynyl, amino loweralkyl, amino loweralkenyl, aminoloweralkynyl, aralkyl;
A and B are joined together to form proline and, the pharmaceutically acceptable salts thereof wherein the aralkyl groups have from one to six carbon atoms in the alkyl portion thereof; aryl, is selected from the group consisting of phenyl, naphthyl or biphenyl; and acyl is a loweralknoyl or aroyl group.

16. The method of claim 15 wherein said compound is a member of the group:
N-(1-carboxy-3-phenylpropyl)-α-azaalanyl-L-proline;
N-[1(S)-carboxy-3-phenylpropyl]-α-azaalanyl-L-proline;
N-(1-carboethoxy-3-phenylpropyl)-α-axaalanyl-L-proline;
N-[1(S)-carboethoxy-3-phenylpropyl]-α-azaalanyl-L-proline;
N-(1-carboethoxy-3phenylpropyl)-α-azaalanyl-L-proline ethyl ester;
N-[1(S)-carboethoxy-3-phenylpropyl]-α-azaalanyl-L-proline ethyl ester;
$N^\alpha$-(1-carboxy-3-phenylpropy)-α-azalysyl-L-proline; and
$N^\alpha$-[1(S)-carboxy-3-phenylpropyl]-α-azalysyl-L-proline.

* * * * *